(12) United States Patent
Le Berre et al.

(10) Patent No.: US 8,785,684 B2
(45) Date of Patent: Jul. 22, 2014

(54) METHANOL CARBONYLATION PROCESS WITH RHODIUM CATALYST, AN IODIDE SALT AND A METALLIC CO-CATALYST SELECTED FROM TRANSITION METALS, INDIUM, STRONTIUM, BARIUM, ZINC, TIN AND HETEROPOLY ACIDS

(71) Applicant: Celanese International Corporation, Irving, TX (US)

(72) Inventors: Carole M. Le Berre, Lacroix-Falgarde (FR); Samuel Gautron, Argelos (FR); Philippe J. Kalck, Auzeville-Tolosane (FR); Philippe G. Serp, Clermont le Fort (FR); Nicolas D. Lassauque, Nice (FR); G. Paull Torrence, League City, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/693,633

(22) Filed: Dec. 4, 2012

(65) Prior Publication Data
US 2013/0102809 A1   Apr. 25, 2013

Related U.S. Application Data

(63) Continuation of application No. PCT/US2010/001698, filed on Jun. 14, 2010.

(51) Int. Cl.
*C07C 51/10* (2006.01)
*C07C 51/12* (2006.01)

(52) U.S. Cl.
USPC .......................................... 562/517; 562/519

(58) Field of Classification Search
None
See application file for complete search history.

(56) References Cited

U.S. PATENT DOCUMENTS

| | | |
|---|---|---|
| 4,894,477 A | 1/1990 | Scates et al. |
| 5,001,259 A | 3/1991 | Smith et al. |

(Continued)

FOREIGN PATENT DOCUMENTS

| | | |
|---|---|---|
| CN | 1105603 | 7/1995 |
| CN | 1345631 | 4/2002 |

(Continued)

OTHER PUBLICATIONS

Howard et al., Science and Technology in Catalysis 1999, "New Acetyls Technologies from BP Chemicals", pp. 61-68.
Ling et al., "Study of the Effects of Rare Earth Metal Additives on Methanol Carbonylation Reaction", Hua Xue Tong Bao [Notes of Chemistry], vol. 68, 2005.

(Continued)

*Primary Examiner* — Karl J Puttlitz
(74) *Attorney, Agent, or Firm* — Michael W. Ferrell; Ferrells, PLLC; Anna L. Kinney

(57) ABSTRACT

A carbonylation process for making acetic acid uses a metallic co-catalyst composition effective as a rhodium stabilizer and rate promoter at molar ratios of metal/rhodium of from about 0.5 to 30. A preferred process includes: (a) reacting methanol with a carbon monoxide feedstock in a rhodium-based catalytic reaction mixture having: (i) a rhodium catalyst metal, (ii) methyl iodide maintained from about 1 to 20 weight percent, (iii) a lithium iodide co-catalyst, (iv) a metallic co-catalyst composition, (v) water maintained from 0.1 weight percent to less than 8 weight percent, (vi) methyl acetate maintained from about 0.5 to about 30 weight percent, and (vii) acetic acid; (b) flashing crude acetic acid from the reaction mixture; and (c) purifying the crude acetic acid. This process achieves stability and a STY greater than 10 mol/L/hr, with substantially less than a theoretically equivalent inorganic iodide content corresponding to the metallic co-catalyst and lithium iodide.

15 Claims, 5 Drawing Sheets

(56) References Cited

U.S. PATENT DOCUMENTS

| | | |
|---|---|---|
| 5,026,908 A | 6/1991 | Smith et al. |
| 5,144,068 A | 9/1992 | Smith et al. |
| 5,218,143 A | 6/1993 | Jones |
| 5,416,237 A | 5/1995 | Aubigne et al. |
| 5,939,585 A | 8/1999 | Ditzel et al. |
| 6,303,813 B1 | 10/2001 | Scates et al. |
| 6,323,364 B1 | 11/2001 | Agrawal et al. |
| 6,657,078 B2 | 12/2003 | Scates et al. |
| 7,005,541 B2 * | 2/2006 | Cheung et al. ............. 562/519 |
| 7,053,241 B1 | 5/2006 | Torrence |
| 7,276,626 B2 | 10/2007 | Gaemers et al. |
| 7,368,597 B2 * | 5/2008 | Gaemers et al. ........... 562/519 |
| 2008/0071110 A1 * | 3/2008 | Chen et al. ................. 562/519 |

FOREIGN PATENT DOCUMENTS

| | | |
|---|---|---|
| CN | 1349855 | 5/2002 |
| CN | 1562937 A | 1/2005 |
| JP | 2005336105 | 12/2005 |
| WO | 2004101487 A1 | 11/2004 |
| WO | 2004101488 A1 | 11/2004 |
| WO | 2006064178 A1 | 6/2006 |

OTHER PUBLICATIONS

Shao et al., "Study of the Effects of Metal Salts on Methanol Carbonylation Reaction", Journal of Molecular Catalysis (China), vol. 18, No. 6, Dec. 2004.

Ullman's Encyclopedia of Industrial Chemistry, "Acetic Acid", vol. A1, pp. 45-64, 5th ed, 1985.

Watson, The Cativa™ Process for the Production of Acetic Acid, Chem. Ind. (Dekker) (1998) 75 Catalysis of Organic Reactions, pp. 369-380.

Pauling L., General Chemistry, "Titanium, Vanadium, Chromium, and Manganese and Their Congeners", Chapter 22 pp. 722-740 Dover (1988).

Kirk-Othmer Encyclopedia of Chemical Technology, "Rare-Earth Elements", Third Edition, vol. 19, pp. 833-854, John Wiley & Sons (1982).

Zhang et al., "Promoting effect of transition metal salts on rhodium catalyzed methanol carbonylation", Catalysis Communications 7 (2006), pp. 885-888.

Qian et al., "Promoting effect of oxometallic acids, heteropoly acids of Mo, W and their salts on rhodium catalyzed methanol carbonylation", Catalysis Communications 8 (2007), pp. 483-487.

* cited by examiner

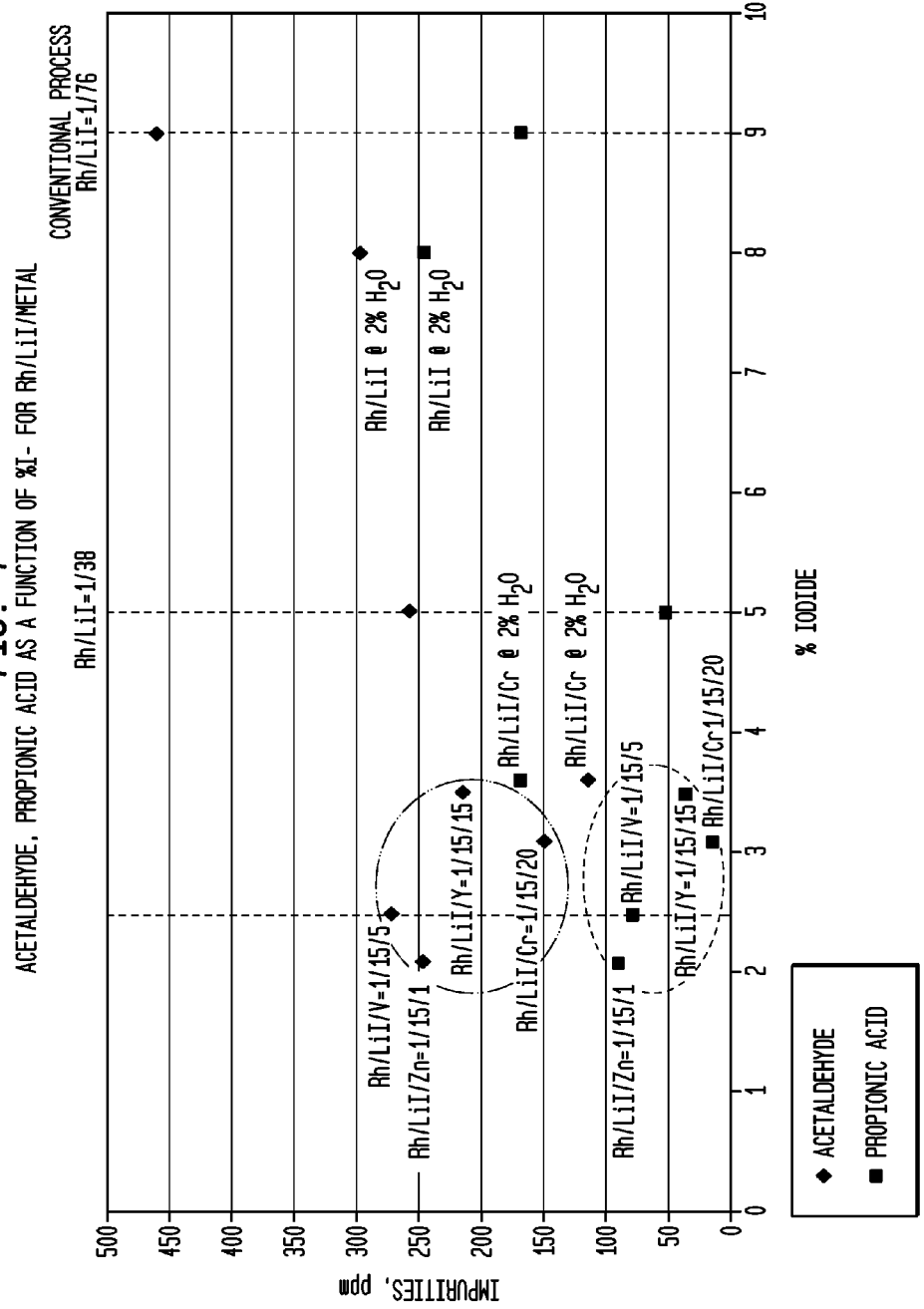

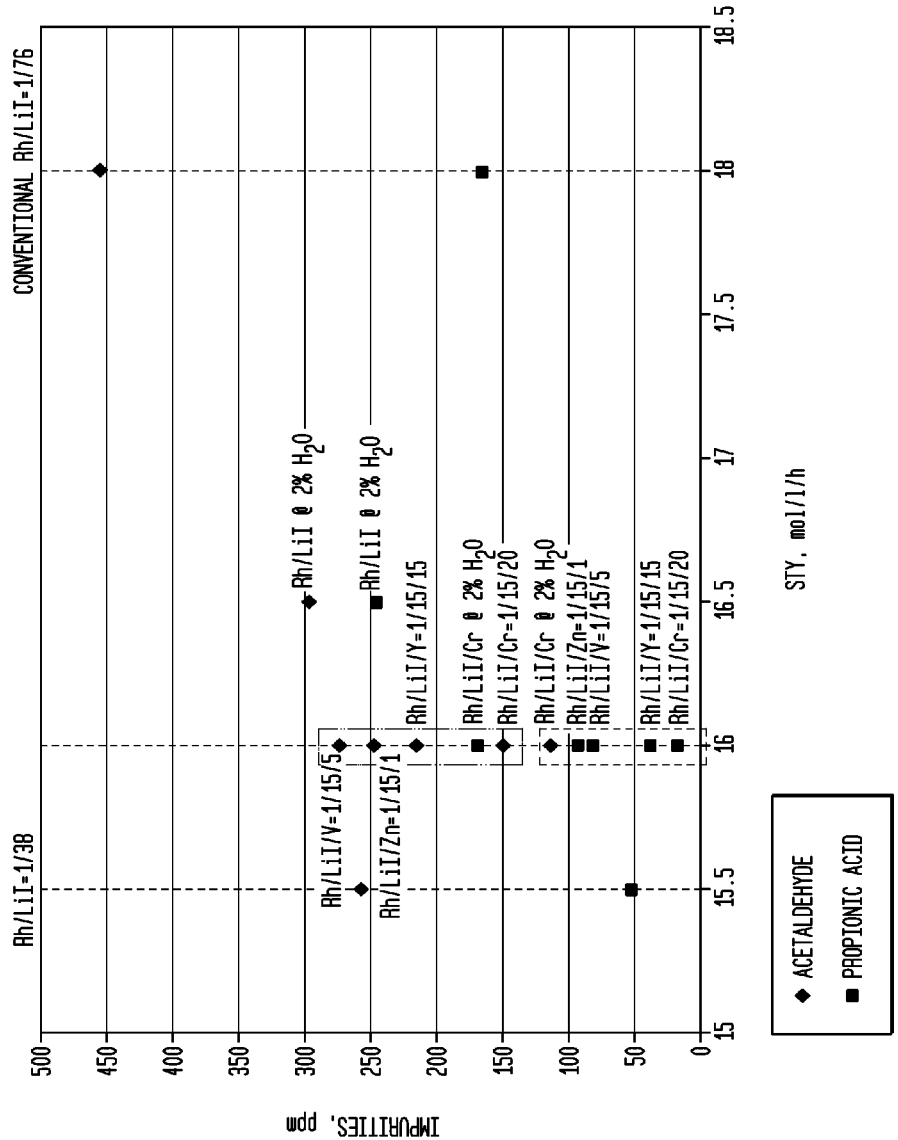

METHANOL CARBONYLATION PROCESS WITH RHODIUM CATALYST, AN IODIDE SALT AND A METALLIC CO-CATALYST SELECTED FROM TRANSITION METALS, INDIUM, STRONTIUM, BARIUM, ZINC, TIN AND HETEROPOLY ACIDS

CLAIM FOR PRIORITY

This application is a national phase entry of International Application No. PCT/US2010/001698, filed Jun. 14, 2010, entitled "Carbonylation Process". The priority of International Application No. PCT/US2010/001698 (PUBLISHED AS WO 2011/159268) is hereby claimed and its disclosure incorporated herein by reference in its entirety.

TECHNICAL FIELD

The present invention relates to methanol carbonylation to make acetic acid using an aqueous homogeneous rhodium catalyst medium with lithium iodide in less than conventional quantities and one or more stabilizing and promoting metals selected and utilized under conditions which generate substantially less than a theoretically equivalent amount of inorganic iodide corresponding to the concentration of metal added. Metal/rhodium molar ratios of from about 0.5:1 to about 30:1 are employed. The process is carried out under low water conditions, suitably from about 0.1-10 wt % water in the reactor. Suitable stabilizing and promoting metals are, for example, tin; zinc; yttrium; a hetero poly acid; chromium; vanadium; or yttrium in combination with zinc.

BACKGROUND

Reaction systems of choice to manufacture acetic acid in high yields, on a large scale with economically viable production rates, include those with a relatively low water (less than 14 wt %) aqueous rhodium catalyst system which includes an iodide salt. See, for example, U.S. Pat. No. 5,144,068 to Smith et al. and U.S. Pat. No. 6,657,078 to Scates et al. So called "low water" processes for making acetic acid have much better carbon monoxide efficiency than conventional Monsanto processes due, in part, to less generation of hydrogen and carbon dioxide by way of the water gas shift reaction.

Commercial systems typically have corrosion metals present in the catalytic medium which result in relatively low levels of iodide salts in the presence of methyl iodide under reaction conditions. In general, conventional wisdom is that corrosion metals (i.e., iron, nickel, chromium, molybdenum, and the like) are not as effective as alkali metals such as lithium in providing inorganic iodide to the system and thereby stabilizing the rhodium catalyst (a significant cost of production) under reduced carbon monoxide pressure as is encountered in a flash vessel. Moreover, corrosion metals have been considered undesirable due to solubility and by-product issues. See U.S. Pat. No. 4,894,477 to Scates et al., Col. 2, line 13 and following, as well as Col. 9, Table 1. As one of skill in the art will be aware, iodide salt containing systems are highly effective as to stabilizing the rhodium from precipitating under reduced carbon monoxide partial pressures as well as maintaining production rates under low water conditions. The rhodium/lithium iodide system has drawbacks, however, notably: (1) the reaction medium is highly corrosive due, in part, to the elevated levels of iodide salt and (2) the rhodium/lithium iodide system tends to generate a plethora of aldehyde-related impurities such as propionic acid, acetaldehyde, crotonaldehyde, higher unsaturated aldehydes, and higher alkyl iodides, all of which are difficult to remove. See Howard et al., Science and Technology in Catalysis 1998, p 64-65 and D. J. Watson, Proceedings of the $17^{th}$ ORCS Meeting, Marcel Dekker (1998) for more information relating to corrosion and impurities.

Ruthenium and other metals have been considered for their ability to promote higher production rates in combination with iodide salts. Chinese Patent No. 1,562,937 to Haojing Chemical Co., Ltd., discloses use of ruthenium as a co-catalyst at a molar ratio to rhodium of 2.9:1, with a water concentration of 3 to 14.5 wt % and a 15.5 wt % iodide concentration at a rhodium concentration of 1000 ppm (see Table 1). U.S. Pat. No. 5,939,585 to Ditzel et al. disclose use of ruthenium or osmium as a promoter (Claim 1) at a molar ratio to rhodium range of 0.1:1 to 20:1 (Col. 3, lines 58-59) and a water concentration of 0.1 to 7 wt %. U.S. Pat. Nos. 7,368,597 and 7,276,626 both to Gaemers et al. (equivalent to WO 2004/101487 and WO/2004/101488, respectively) show the use of osmium, rhenium, cadmium, mercury, tungsten, ruthenium or zinc as a rate promoter (¶ 0059) at a molar ratio to rhodium of 0.1:1 to 20:1 (¶ 0069) with a water concentration of 0.1 to 30 wt % (¶ 0081). Gaemers et al. also disclose the use of iodide complexes of lanthanide metals, molybdenum, nickel, iron and chromium as stabilizers (¶ 0070). However, Gaemers et al. primarily rely on a ligand to impart catalyst stability.

Other references likewise disclose the use of additional metals in a rhodium/iodide catalyst system for making acetic acid. U.S. Pat. No. 7,053,241 to Torrence discloses the use of tin or ruthenium in a range of molar ratios to rhodium of 0.1:1 to 20:1 (Abstract) at a water concentration of 0.1 to 14 weight % (Col. 4, lines 7-15). The process disclosed in Torrence '241 includes the presence of an iodide ion concentration greater than about 3 wt % as does most of the literature discussing metal promoters/stabilizers in a methanol carbonylation process at water concentrations of less than 14% by weight. United States Publication No. 2008/0071110 to Chen et al., now U.S. Pat. No. 7,671,233, for example, show use of lanthanides, copper, titanium, zirconium, vanadium, manganese, cobalt, palladium, tin, chromium, nickel, molybdenum, or zinc (¶ 0014) as a promoter in a range of molar ratios to rhodium of about 0.1:1 to about 7:1 (¶ 0016 and Examples) at a water concentration of 1 to 14 weight %. Chen et al. also discuss the use of yttrium in a molar ratio to rhodium range of 0.09:1 to 5:1 without another stabilizing component; however, in virtually all cases, significant iodide levels are reported and the apparent intended function of the metal promoter/stabilizer is to stabilize inorganic iodide concentration which, in turn, stabilizes the catalyst solution.

Japanese Kokai Patent Application 2005-336105 to Daicel Chemical Industries Ltd., now Japanese Patent No. JP 4657632 B2, discloses a method for manufacturing carboxylic acid in the presence of a rhodium catalyst, lithium iodide at a concentration of 0.1 to 30 wt %, a limited amount of water (15 wt % or less), and at least one element or element-containing compound selected from Zn (in a concentration of 10-5,000 ppm), Sn, Ge, and Pb (in concentrations of 10-20,000 ppm). U.S. Pat. No. 5,218,143 to Jones shows rhodium catalyzed carbonylation with 0.5 to 5 wt % water stabilized with lithium iodide (2-20 wt %; approximately 120:1 to 1200:1 Li:Rh molar ratio) and a Group VI B metal costabilizer, i.e., chromium, molybdenum, or tungsten, in a concentration of 0-10,000 ppm which corresponds to a metal:Rh molar ratio of approximately 0:1 to 276,000:1. The lithium iodide concentrations of Jones are significantly higher than those of the present invention.

Still other metal iodides have been considered as alternative stabilizers to lithium iodide. For instance, U.S. Pat. No.

5,416,237 to Aubigne et al. discloses use of beryllium iodide as a stabilizer, (Col. 3, lines 43-49) using up to 10 weight % water.

Various alternatives to rhodium/lithium iodide systems have been suggested based on laboratory batch unit data, typically including relatively low levels of metal salts, generally at equimolar amounts with rhodium or less. In this regard, see Zhang et al., "Promoting effect of transition metal salts on rhodium catalyzed methanol carbonylation", Catalysis Communications 7 (2006), pp. 885-888; Ling et al., "Study of the Effects of Rare Earth Metal Additives on Methanol Carbonylation Reaction", Hua Xue Tong Bao [Notes of Chemistry], Vol. 68, 2005; and Shao et al., "Study of the Effects of Metal Salts on Methanol Carbonylation Reaction", Journal of Molecular Catalysis (China), Vol. 18, No. 6, December, 2004. So also, it has been suggested to use heteropoly acids of molybdenum and tungsten with rhodium catalysts to make acetic acid, also at relatively low metal concentrations. See Qian et al., "Promoting effect of oxometallic acids, heteropoly acids of Mo, W and their salts on rhodium catalyzed methanol carbonylation", Catalysis Communications 8 (2007), pp. 483-487. All four documents provide experimental data derived from a batch process, with results determined as soon as 5 minutes into the reaction. These data do not predict results in a continuous process at equilibrium, nor does the data supply information concerning the stability of the catalyst system at reduced carbon monoxide pressure as is seen in a flash vessel of a production unit. With respect to Zhang et al., it is noted that, although metal:rhodium molar ratios (Cr, Fe, Ni, and Zn) of from 2.4 to 4.7 were considered (Table 1), the rate data were determined after 5 minutes. Similarly, with regard to Ling et al., the reaction times were no higher than 55 minutes (Table 1), and only consider a single promoter molar ratio of 1:1 (Nd, Ce, or La:Rh). Furthermore, Shao et al. again provided data after only 10 minutes of reaction time (FIG. 1) for metal:rhodium (Sn, Pb, Cr, and Zr) molar ratios of 0.5:1 to 2.5:1. Note that the tin promoter used was $SnCl_2$. Finally, Qian et al. provided data collected after 5 minutes of reaction time (page 484) for HPA:rhodium molar ratios of from 0.2:1 for phosphotungstic acid (PTA) and sodium phosphotungstate (SPT) to 6:1 for $Na_2MoO_4$. In any event, the various papers referred to in this paragraph appear to be directed to identifying metals or metal-containing compositions which provide a substantial iodide concentration to stabilize the rhodium catalyst.

WIPO Publication WO 2006/064178 to BP Chemicals Limited teaches a catalyst system for the production of acetic acid which comprises a rhodium carbonylation catalyst, methyl iodide, and at least one non-hydrohalogenoic acid promoter, such as a heteropoly acid, in the presence or absence of alkali metal iodides, alkaline earth iodides or other components, such as amines or phosphine derivatives, recognized as capable of generating $I^-$ by reaction with alkyl iodides such as methyl iodides. The WO '178 publication teaches to optionally include a copromoter capable of generating ionic iodide such as lithium iodide, lanthanide metals, nickel, iron, aluminum, and chromium. It is seen in the Examples which follow that chromium, for example, may be used in accordance with the present invention without forming inorganic iodide at or near theoretically equivalent amounts corresponding to the concentration of chromium added, contrary to the teachings of the WO '178 publication.

As the methanol carbonylation process has been practiced at increasingly lower water concentrations other problems have been found to have arisen. Specifically, operating at this new lower water regime has exacerbated certain impurities in the product acetic acid. As a result, the acetic acid product formed by the above-described low water carbonylation is frequently deficient with respect to the permanganate time owing to the presence therein of small proportions of residual impurities. Since a sufficient permanganate time is an important commercial test which the acid product must meet for many uses, the presence therein of such impurities that decrease permanganate time is objectionable [Ullman's Encyclopedia of Industrial Chemistry, "Acetic Acid", Volume A1, p. 56, $5^{th}$ ed]. Of particular concern are certain carbonyl compounds and unsaturated carbonyl compounds, particularly acetaldehyde and its derivatives, crotonaldehyde and 2-ethyl crotonaldehyde (also referred to as unsaturated aldehyde impurities). However, other carbonyl compounds known also to affect the permanganate time are acetone, methyl ethyl ketone, butyraldehyde, and 2-ethyl butyraldehyde. Thus, these carbonyl impurities affect the commercial quality and acceptability of the product acetic acid. If the concentration of carbonyl impurities reaches only 10-15 ppm, the commercial value of the product acetic acid will certainly be negatively affected. As used herein the phrase "carbonyl" is intended to mean compounds which contain aldehyde or ketone functional groups which compounds may or may not possess unsaturation.

It is postulated in an article by Watson, The Cativa™ Process for the Production of Acetic Acid, Chem. Ind. (Dekker) (1998) 75 Catalysis of Organic Reactions, pp. 369-380, that enhanced rhodium catalyzed systems have increased standing levels of rhodium-acyl species which will form free acetaldehyde at a higher rate. The higher rate of acetaldehyde formation can lead to the increased production of permanganate reducing compounds.

The precise chemical pathway within the methanol carbonylation process that leads to the production of crotonaldehyde, 2-ethyl crotonaldehyde and other permanganate reducing compounds is not well understood. One prominent theory for the formation of the crotonaldehyde and 2-ethyl crotonaldehyde impurities in the methanol carbonylation process is that they result from aldol and cross-aldol condensation reactions starting with acetaldehyde. Because theoretically these impurities begin with acetaldehyde, many previously proposed methods of controlling carbonyl impurities have been directed towards removing acetaldehyde and acetaldehyde-derived carbonyl impurities from the reaction system. So also, operation at reduced hydrogen partial pressure and/or reduced methyl iodide has been proposed. See U.S. Pat. No. 6,323,364 to Agrawal, et al., as well as U.S. Pat. No. 6,303,813 to Scates et al., the disclosures of which are incorporated herein by reference.

Conventional techniques used to remove acetaldehyde and carbonyl impurities have included treatment of acetic acid with oxidizers, ozone, water, methanol, amines, and the like. In addition, each of these techniques may or may not be combined with the distillation of the acetic acid. The most typical purification treatment involves a series of distillations of the product acetic acid. Likewise, it is known to remove carbonyl impurities from organic streams by treating the organic streams with an amine compound such as hydroxylamine which reacts with the carbonyl compounds to form oximes followed by distillation to separate the purified organic product from the oxime reaction products. However, this method of treating the product acetic acid adds significant cost to the process.

Despite much effort and substantial need in the art for an improved low water, rhodium catalyzed methanol carbonylation process without elevated levels of inorganic iodide, little progress has been made and the rhodium/lithium iodide system remains the system of choice for commercial production because of the rhodium stability provided under reduced carbon monoxide pressure as is seen in the flasher of a continuous production unit.

SUMMARY OF INVENTION

We have unexpectedly found that by judicious choice of a transition metal (or selected other metal) co-catalyst composition effective as a stabilizer and promoter and utilizing the metals in specified molar ratios with rhodium, that a low water acetic acid process can be operated with inorganic iodide concentrations that are substantially lower than the theoretically equivalent amount correspondent to the concentration of the added metals, while preserving catalyst stability and achieving high rates. The results are surprising in view of conventional wisdom in the art that a substantial inorganic iodide content must be provided under low water conditions in order to prevent precipitation of rhodium in the form of rhodium triiodide because of low levels of hydriodic acid (HI) in equilibrium with methyl iodide at low water levels. Iodide salts are also rate promoters which make conventional systems employing them economically attractive. Further, one of skill in the art would have expected inorganic iodide concentrations in the reaction mixture due to addition of stabilizer and promoter metals to be substantially equivalent with the metals present; e.g., that approximately three moles of inorganic iodide would be present for every mole of trivalent metal added.

We have unexpectedly found that lithium iodide in combination with low concentrations of chromium, a heteropoly acid, vanadium, zinc, yttrium, or yttrium and zinc combined, provide effective stabilization and rate promotion at reduced lithium iodide concentrations, even at low water concentrations.

Particularly surprising features of the present invention include that certain metals and combinations thereof provide both (1) rhodium stability under low water conditions especially where reduced carbon monoxide partial pressure is encountered and (2) elevated acetic acid production rates under low water conditions, without maintaining elevated levels of inorganic iodide in the system. The rate promoting and stabilizing compositions may even be added as metal iodides if so desired; there may be little substantial additional inorganic iodide in the system due to the addition of such compounds. It is believed that the iodide added in such cases is primarily consumed in the system by equilibria, producing methyl iodide and resulting in higher levels of metal acetates which provide catalyst stability and promote production rates.

The benefits of the invention are at least three-fold. First, the low inorganic iodide levels make the catalyst system less corrosive than conventional low water catalyst systems, reducing or eliminating corrosion problems. Metallurgy requirements for equipment are also less stringent. Thus, capital and operating costs are reduced. Second, many of the impurity issues arising from elevated levels of inorganic iodide in the system may be ameliorated or overcome. Without intending to be bound by theory, it is believed that many of the impurities are derived from acetaldehyde, as noted above, which appears to form more readily in the presence of iodide salts, for example lithium iodide. Acetaldehyde is believed to condense to form unsaturated aldehydes, such as crotonaldehyde, which then generate higher alkyl iodides in the system which are particularly difficult to remove. So also, acetaldehyde formation appears to cause increases in propionic acid levels because of the availability of hydrogen in the reactor. As inorganic iodide levels are lowered in accordance with the invention, acetaldehyde and related impurities are reduced.

A third benefit arises from the increased production rates at low water conditions. Without intending to be bound by theory, the metallic co-catalyst composition in the presence of very low inorganic iodide accelerates the reductive elimination step of acetyl iodide from the catalyst complex. Consider, for example, a typical depiction of the catalytic cycle in an acetic acid process as shown in the attached FIG. 1, wherein one of skill in the art will appreciate that modification of kinetics of the various reactions will improve production rates and quality. In particular, accelerating the reductive elimination step increases production rates of acetic acid and reduces the opportunity for aldehyde formation from the rhodium complex, resulting in a reduction of acetaldehyde-derived impurities in the final product. Such impurities are difficult, if not impossible to remove without extraordinary purification effort.

Still further features and advantages of the invention are apparent from the following description.

BRIEF DESCRIPTION OF DRAWINGS

The invention is described in detail below with reference to the appended drawings. In the Figures:

FIG. 4 is a graphical depiction of impurities produced during carbonylation (at 5 wt % water except as noted) using metal compositions with reduced levels of lithium iodide as a function of iodide concentration; and FIG. 5 is a graphical depiction of impurities produced during carbonylation (at 5 wt % water except as noted) using metal compositions with reduced levels of lithium iodide as a function of production rate.

DETAILED DESCRIPTION

Figure 1:
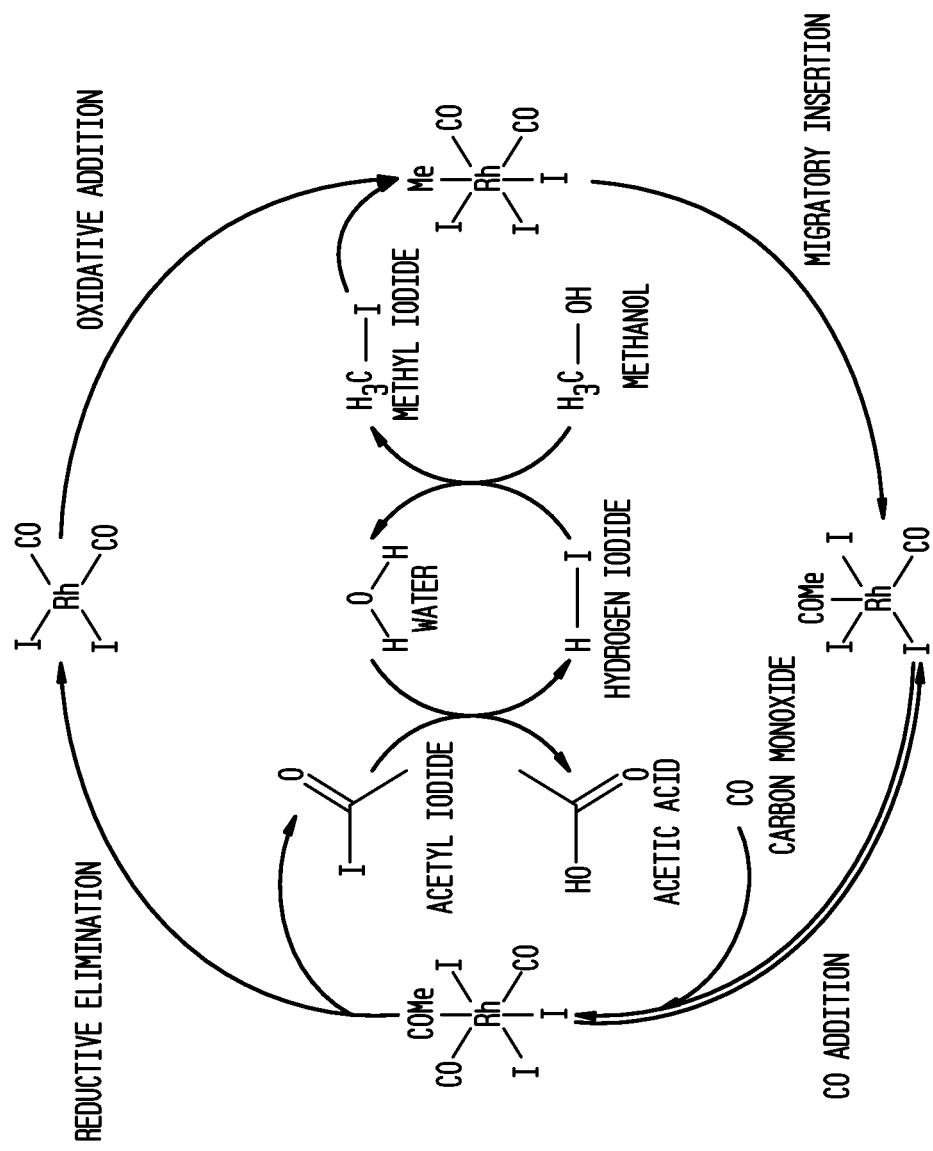
FIG. 1 is a schematic illustrating interrelated reaction paths for a typical methanol carbonylation process.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Ratios refer to molar ratios, %, ppm and like terms refer to weight percent, parts per million by weight and so forth, unless otherwise indicated.

When we refer to reaction mixtures or catalyst systems "consisting essentially of" certain components, we mean to exclude other components that would alter the basic and novel characteristics of the composition, that is, substantially change its reactivity, stability or selectivity. The language "consisting essentially of" specifically excludes unlisted salts in substantial amounts, for example, but does not exclude impurities, by-products, diluents, and so forth.

For present purposes, a metallic co-catalyst composition is considered effective as a rhodium stabilizer in the process at a given water concentration if essentially none of the rhodium catalyst metal precipitates under processing conditions in the flasher of the reaction section of a carbonylation system for a time sufficient to show characteristic stability. To test for stability, a reaction mixture may be tested under a nitrogen atmosphere in a sealed pressure glass tube at 125° C., to simulate the CO partial pressure in the flasher unit. Details of the preparation and procedure appear in U.S. Pat. No. 7,053, 241, the disclosure of which is incorporated herein by reference. In this test, sealed pressure glass tubes are equipped with controlled temperature and stirring using a pressure tube reactor system. The catalyst solutions are purged with carbon monoxide (CO) at 125° to 150° C. and a pressure of 241.1 kPa with stirring for one hour to ensure complete dissolution of the rhodium catalyst complex before conducting catalyst precipitation tests. The prepared catalyst solutions are cooled and then purged with $N_2$ for one hour to remove dissolved CO before placing the catalyst solutions into glass tubes which are sealed under a $N_2$ atmosphere. The rhodium concentration is determined by atomic absorption (AA) spectroscopy. The rhodium concentration of the solution is measured 10 minutes after the nitrogen purge is complete, or longer if so desired. Characteristic stability can also be measured by this method after 30 minutes, 1 hour, 12 hours, 24 hours, 48 hours, or more if so desired. If less than 0.5%, and preferably 0, of the rhodium precipitates, the system is considered stable, and the metal composition is deemed effective as a rhodium stabilizer. Alternatively or as additional indicia of stability, the process may be run under continuous conditions in a carbonylation unit including a flasher, preferably for 5 to 6 hours, and the flasher visually inspected for precipitation. In the experiments discussed herein, turnover in the flasher was 7.5 minutes, which is an appropriate benchmark time for stability under reduced CO partial pressure. Typically, a composition that acts primarily as a stabilizer presents a trend of decreased space-time yield in response to increased molar ratio of the metal in the composition to rhodium in the system. An increase in the molar ratio of a co-catalyst which is only a stabilizer results in an observed decrease of the space-time yield because of stabilization of rhodium by the co-catalyst, which induces a decrease of the activity of rhodium.

In some embodiments, the determination of stability is performed in a system having an amount of lithium iodide insufficient to provide stability alone. For example, an amount of lithium iodide providing a lithium:rhodium molar ratio of 38:1 represents about half of the conventional amount, and cannot provide catalyst stability at this concentration, as shown in the examples (i.e., "unstable").

A metal composition is considered effective as a rate promoter if the carbonylation rate (space-time yield, or STY defined as the g-mole acetic acid product per volume of reactor solution per time (g-mole/L/hr)) measured in acetic acid production is greater than that of the same composition without the promoter component or components. The carbonylation rate is also referred to herein as reaction productivity. Generally, to determine effectiveness of the promoter, the catalytic system is compared to a like catalyst system with the same amount of rhodium alone as the catalyst metal. In some embodiments, the catalytic system is compared to a like catalyst system with the same amount of lithium iodide co-catalyst and rhodium catalyst metal. Additional acetic acid is added to 100%. Typically, a composition that acts primarily as a rate promoter, or activator, presents a trend of increased space-time yield in response to increased molar ratio of the metal in the composition to rhodium in the system.

As used herein, a transition metal includes Group IIIB to Group IIB metals; suitable transition metals include titanium, vanadium, chromium, manganese, iron, cobalt, nickel, copper, yttrium, zirconium, molybdenum, ruthenium, lanthanum, hafnium, tungsten, and platinum. The metals of interest to this case are the transition metals discussed above as well as zinc, beryllium, aluminum, strontium, indium, tin, barium, and bismuth as well as HPA compounds discussed further below. The precise form in which a metal is used is not particularly important, provided that it is effective as a rate promoter and stabilizer, as discussed above.

As used herein, HPA refers to heteropoly acids, a class of complex proton acids made up of a metal, oxygen, an element generally from the p-block of the periodic table, and acidic hydrogen atoms. HPAs are strong Brönsted acids. A heteropoly acid is formed by condensation of two or more inorganic oxyacids comprising a coordinated element (poly atom) and a central element (hetero atom). Typically, from two to eighteen poly atoms, oxygen-linked polyvalent metal atoms, surround one or more hetero atoms. The hetero atom in the heteropoly acid may be one or more of copper, beryllium, zinc, nickel, phosphorus, silicon, boron, aluminum, germanium, gallium, iron, cerium, cobalt, arsenic, antimony, bismuth, chromium, tin, titanium, zirconium, vanadium, sulfur, tellurium, manganese, platinum, thorium, hafnium, or iodine, and the polyatom may be one or more of molybdenum, tungsten, vanadium, chromium, niobium, or tantalum, but these examples are not intended to be limiting. These acids include, but are not limited to, phosphomolybdic acid ($H_3[PO_4(Mo_2O_6)_6].xH_2O$) also known as PMA, tungstosilicic acid ($H_4SiW_{12}O_{40}.xH_2O$), tungstophosphoric acid ($H_3[P(W_3O_{10})_4].xH_2O$) also known as PTA, molybdosilicic acid ($H_4SiMo_{12}O_{40}.xH_2O$), molybdophosphoric acid ($H_3PMo_{12}O_{40}.xH_2O$), molybdotungstophosphoric acid ($H_3[PMo_nW_{12-n}O_{40}].xH_2O$), molybdotungstosilicic acid ($H_4[SiMo_nW_{12-n}O_{40}].xH_2O$), vanadotungstophosphoric acid ($H_{3+n}[PV_nW_{12-n}O_{40}].xH_2O$), vanadotungstosilicic acid ($H_{4+n}[SiV_nW_{12-n}O_{40}].xH_2O$), vanadomolybdosilicic acid ($H_{4+n}[SiV_nMo_{12-n}O_{40}].xH_2O$), vanadomolybdophosphoric acid ($H_{3+n}[PV_nMo_{12-n}O_{40}].xH_2O$, wherein n is an integer of 1 to 11 and x is an integer of 1 or more), tungstoboric acid ($H_5BW_{12}O_{40}$), molybdoboric acid ($H_5BMo_{12}O_{40}$) and molybdotungstoboric acid ($BH_5Mo_6O_{40}W_6$). The structures of some of the well known anions are named after the original researchers in this field. The first characterized and the best known of these is the Keggin heteropolyanion, typically represented by the formula $XM_{12}O_{40}^{x-8}$, where X is the central atom ($Si^{4+}$ or $P^{5+}$), x is its oxidation state and M is the metal ion ($Mo^{6+}$ or $W^{6+}$).

Preferably, the HPA selected comprises a phosphorus or silicon hetero atom and at least one polyatom selected from the group consisting of tungsten, molybdenum, chromium, vanadium and tantalum. The preferred HPAs may be represented by the formula $H_3M_{12}XO_{40}$, where M is the polyatom, and X is the hetero atom. Especially preferred HPAs comprise polyatoms selected from tungsten and molybdenum.

In some embodiments, a metallic co-catalyst composition is a composition comprising a lanthanide-series metal, metal compound, or metal complex. Lanthanide series metals, or lanthanons, include lanthanum, cerium, praseodymium, neodymium, promethium, samarium, europium, gadolinium, terbium, dysprosium, erbium, thulium, ytterbium, and lutetium. The precise form in which a metal is used is not particularly important, provided that it is effective as a rate promoter and stabilizer, as discussed above.

A rhodium-based catalyst system refers to a system providing a rhodium metal catalyst and an iodide promoter in a carbonylation reaction mixture.

An aqueous reaction mixture refers to a carbonylation reaction mixture comprising, for instance, water, a rhodium-based catalyst, methanol and/or methyl acetate, methyl iodide, a co-catalyst, and acetic acid.

As used herein, "reductive elimination" refers to a catalytic reaction step of a mechanistic catalyst cycle whereby the rhodium acyl carbonyl iodide complex, $[Rh(CO)_2I_3(COCH_3)]^{1-}$, eliminates acetyl iodide from the complex to form acetyl iodide and regenerates the rhodium catalyst, $[Rh(CO)_2I_2]^{1-}$.

As used herein, "correspondent inorganic iodide" and like terminology refers to inorganic iodide attributable to the stabilizing and promoting metals added to the system in accordance with the invention. Total inorganic iodide is measured in a reaction medium by titration with an aqueous solution of silver nitrate at room temperature. Titration with silver nitrate yields a value for total inorganic halides which often consists primarily of inorganic iodides in a system according to the invention. The measurement is corrected for equilibrium HI levels and inorganic iodides attributable to any corrosion metal iodides which may be present. That is, inorganic iodide levels due to HI and corrosion metal iodides are subtracted from total iodides to determine levels of correspondent inorganic iodide attributable to the stabilizing and promoting metals added to the system in accordance with the invention. In some embodiments, total inorganic iodide is attributable to both the stabilizing and promoting metals and the reduced lithium iodide content of the reaction mixture. For present purposes "substantially less than a theoretically equivalent inorganic iodide content corresponding to the presence of a metallic co-catalyst" and like wording refers to a reaction mixture in which a metal added as a co-catalyst contributes substantially less than a theoretically equivalent amount of inorganic iodide determined by assuming that all the metal added would form a metal-iodide ionic compound. For instance, a system in accordance with the invention in which chromium is used as a stabilizing and promoting metal would result in a reaction mixture containing substantially less than three moles of inorganic iodide for each mole of chromium added (based on a $Cr^{3+}$ oxidation state). Such a reaction mixture would generally provide an actual inorganic iodide concentration upon titration of less than 75%, 70%, 65%, or 60% of the theoretically equivalent inorganic iodide concentration, and typically less than 55% or less than 50% of the theoretically equivalent inorganic iodide concentration. The reaction mixture would preferably have an actual inorganic iodide concentration of less than 40%, less than 35%, or less than 30% of the theoretically equivalent inorganic iodide concentration, and more preferably less than 20% of the theoretically equivalent inorganic iodide concentration. Even more preferably, the reaction mixture would have an actual inorganic iodide concentration of less than 15% of the theoretically equivalent inorganic iodide concentration. An inorganic iodide content of less than 90% or 80% of the equivalent amount corresponding to the metal co-catalyst added may be considered a substantial reduction in some cases.

Generally, in most cases, a concentration of correspondent inorganic iodide due to the presence of the metallic co-catalyst composition is maintained in the reactor below 5 wt % or below 4 wt %. In some embodiments, the concentration of correspondent inorganic iodide is due to the presence of the metallic co-catalyst composition and low levels of lithium iodide. Typically, the concentration of correspondent inorganic iodide due to the presence of the metallic co-catalyst composition is maintained in the reactor below 3.5 wt % or below 3 wt %. Preferably, the concentration of correspondent inorganic iodide due to the presence of the metallic co-catalyst composition is maintained in the reactor below 2.5 wt % or below 2 wt %. More preferably, the concentration of correspondent inorganic iodide due to the presence of the metallic co-catalyst composition is maintained in the reactor below 1.5 wt %. The present invention is advantageously practiced with less than 3% or less than 2% or so total inorganic iodides present in the reaction mixture from sources other than the rhodium stabilizing and rate promoting metal composition in any event to ameliorate corrosion problems and generation of undesirable by-products as noted above.

A rhodium metal catalyst may be added in any suitable form such that rhodium is in the catalyst solution as an equilibrium mixture including $[RhI_2(CO)_2]^{1-}$, as is well known in the art. When rhodium solution is in the carbon monoxide-rich environment of the reactor, solubility of the rhodium is generally maintained because rhodium/carbonyl iodide species are generally soluble in water and acetic acid. However, when transferred to carbon monoxide depleted environments as typically exist in the flasher, light ends column and so forth, the equilibrium rhodium/catalyst composition changes since less carbon monoxide is available; rhodium catalyst precipitates.

An alkyl halide, preferably methyl iodide co-catalyst/promoter (also referred to herein as an iodide promoter) is generally used in combination with the Group VIII metal catalyst component. Methyl iodide is preferred as the alkyl halide promoter. Preferably, the concentration of alkyl halide in the liquid reaction composition is in the range 1 to 50% by weight, preferably 2 to 30% by weight.

While it is preferable in most circumstances to operate with the lowest possible level of inorganic iodide, in some embodiments it is possible to operate with additional inorganic iodide which may be added in the form of iodide salts or provided by way of appropriate precursors, for example lithium acetate, as is known in the art. In most cases, the iodide salts or other inorganic iodide (anion)-generating species provide inorganic iodide in substantially a theoretical amount, as is described herein. The inorganic iodide may be generated in-situ, since under the operating conditions of the reaction system, a wide range of non-iodide precursors will react with methyl iodide to generate inorganic iodide, which acts as a catalyst stabilizer. For additional detail regarding iodide salt generation, see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference. Added or generated in-situ inorganic iodide may be used in connection with this invention as a co-catalyst or co-stabilizer with a metal co-stabilizer, but at a reduced concentration of inorganic iodide in comparison with conventional carbonylation. The inorganic iodide-providing co-catalyst may be provided in the form of a soluble salt of an alkali metal or alkaline earth metal or a quaternary ammonium or phosphonium salt. In certain embodiments, the catalyst stabilizer/co-promoter is lithium iodide, lithium acetate, or mixtures thereof. The inorganic iodide may be added as a mixture of compounds, such as a mixture of lithium iodide and sodium iodide and/or potassium iodide. See U.S. Pat. Nos. '259; '908; and '068, all to Smith et al., as referred to above. Alternatively, the inorganic iodide may be added as a precursor which generates inorganic iodide in-situ under the operating conditions of the reaction system. A wide range of non-iodide precursors which are useful include alkali metal acetates and carboxylates which will react with methyl iodide and/or HI to generate a predetermined level of inorganic iodide. The appropriate level of inorganic iodide may also be generated in-situ from non-ionic or neutral precursors, such as a phosphine oxide, arsenes, phosphines, amines, amino acids, sulfides, sulfoxides or any suitable organic ligand or ligands if so desired. Phosphine oxides, phosphines, amines, amino acids or other nitrogen or phosphorous containing compounds and suitable organic ligands generally undergo reaction readily in the presence of methyl iodide and/or HI at elevated temperatures to yield and maintain a specific level of inorganic iodide anion concentration in the reaction mixture. Useful non-iodide precursors are thus defined by their ability to maintain elevated inorganic iodide anion levels, rather than by the form in which they are added to the system. One way of introducing inorganic iodide is by incorporating suitable neutral or ionic precursor moieties such as ligands into a rhodium catalyst system as separate entities or complexed with rhodium (typically monodentate or bidentate ligands). In either case, under carbonylation conditions in the presence of methyl iodide, these free ligands, or these ligands complexed with rhodium, decompose and/or react with methyl iodide and/or HI to provide elevated levels of inorganic iodide anions. In this regard, the following Chinese References are of particular interest: Chinese Publication CN1345631; Application No. 00124639.9; Chinese Publication No. CN1105603; Application No. 94100505.4; and Chinese Publication No. CN1349855; Application No. 00130033.4. Suitable rhodium catalyst complexes which provide inorganic iodide as a co-stabilizer/promoter thus include complexes having the following structures:

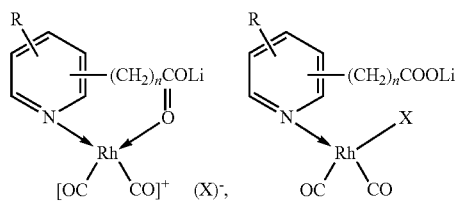

wherein R is H, or a carboxyl-containing hydrocarbon derivative; $(X^-)$ is $BPh_4^-$, $BF_4^-$, or $CH_3COO^-$; X is I, Cl, or Br; and n=0, 1, or 2. Other compounds useful as inorganic iodide-providing co-catalysts include pyridine derivatives such as:

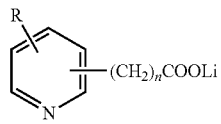

wherein R is H, or a carboxyl-containing hydrocarbon derivative, and n is 0, 1, or 2. Preferably, R is H, or e.g., lithium pyridine-2-formate, lithium pyridine-3-formate, lithium pyridine-4-formate, lithium pyridine-2-acetate, lithium pyridine-3-acetate, lithium pyridine-4-acetate, or lithium pyridine-3-propionate. One of skill in the art will appreciate that a great many other components may be used to generate inorganic iodide.

The metallic co-catalyst compositions of the invention may be added to the reaction mixture in any suitable form, preferably wherein the promoter metal is in a non-zero oxidation state. Following are exemplary chromium salts: $Cr(OH)_3 \cdot 3H_2O$, $CrCl_2$, $CrCl_3 \cdot 6H_2O$, $CrI_2$, $CrBr_2$, $CrI_3 \cdot 9H_2O$, $CrBr_3 \cdot 6H_2O$, $CrO_3$, $Cr_2O_3$, $CrPO_4 \cdot 6H_2O$, $Cr(OCOCH_3)_3$, $Cr(NO_3)_3 \cdot 9H_2O$, $CrCO_3$, $Cr(OCOCH_3)_2$. Further details as to suitable chromium compounds are found in Pauling L., General Chemistry, Chapter 22 pp. 722-740 Dover (1988), the disclosure of which is incorporated herein by reference. Similar forms are suitable for nickel, iron, molybdenum, bismuth, tin, zinc, yttrium, lanthanum, and beryllium. Exemplary lanthanum salts include: $La(C_2H_4O_2)_3 \cdot H_2O$; LaSb; LaAs; $LaI_3$; $La_2(CO_3)_3 \cdot 8H_2O$; $La_2(O:C_6Cl_2O_2:O)_3 \cdot xH_2O$; $LaCl_3 \cdot 7H_2O$; $LaF_3$; $La(NO_3)_3 \cdot 6H_2O$; $La_2(C_2O_4)_3 \cdot 9H_2O$; $La_2O_3$; LaP; and $La_2(SO_4)_3 \cdot 9H_2O$. Similar forms are suitable for cerium, praseodymium, neodymium, and the remaining lanthanide series metals. Further details as to suitable lanthanide compounds are found in the Kirk-Othmer Encyclopedia of Chemical Technology, Third Edition, Vol. 19, pp. 833-854, John Wiley & Sons (1982). All precursors capable of forming the active species are preferred. Acetate, chloride, iodide, carbonyl, and nitrate forms are particularly preferred.

A preferred carbonylation apparatus or process generally includes at least a reactive section, including a reactor and a flash vessel, and a purification section. The apparatus of the present invention is used in connection with the carbonylation of methanol, and/or its reactive derivatives, with carbon monoxide in a homogeneous catalytic reaction system comprising a reaction solvent (typically acetic acid), methanol and/or its reactive derivatives, a soluble rhodium catalyst and at least a finite concentration of water. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in-situ by the water gas shift reaction is preferably kept low, for example, less than 1 bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure in the carbonylation reactor is suitably in the range 10 to 200 bar, preferably 10 to 100 bar, most preferably 15 to 70 bar. The temperature of the carbonylation reaction is suitably in the range 100 to 300° C., preferably in the range 125 to 220° C. Acetic acid is manufactured in a liquid phase reaction at a temperature of from about 150-200° C. and a pressure of from about 30 to about 60 bar in typical embodiments wherein acetic acid is utilized in the reaction mixture as the solvent for the reaction.

The reaction mixture is fed to a flash vessel at reduced pressure to flash off product and light ends. The pressure in the flash vessel is generally less than 2 or 3 bar and usually less than 1 bar. Less than 1 bar carbon monoxide partial pressure is also typical in the flash vessel. Less than 0.5 bar or 0.25 bar carbon monoxide partial pressure is used in flash vessels of commercial production units.

Suitable reactive derivatives of methanol include methyl acetate and dimethyl ether. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 1 to 70% by weight, preferably 1 to 50% by weight, most preferably 2 to 35% by weight.

Water may be formed in-situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water in the liquid reaction composition is in the range 0.1 to 16% by weight, more preferably 0.1 to 14% by weight, even more preferably 0.1 to 10% by weight, and most preferably 1 to 8% by weight. In some embodiments, the concentration of water in the liquid reaction composition is generally in the range of 0.1 to 10 wt %, typically 0.2 to 5 wt %, preferably 0.5 to 3 wt %, more preferably 0.5 to 2.5 wt %, even more preferably 0.75 to 2.5 wt %, and most preferably 1.5 to 2.5 wt %.

The reaction liquid is typically drawn from the reactor and flashed. The crude vapor product stream from the flasher is sent to a purification system which generally includes a light ends column and a dehydration column, and optionally further purification if required. The carbonylation system may use only 2 purification columns and is preferably operated as described in more detail in U.S. Pat. No. 6,657,078 to Scates et al., entitled "Low Energy Carbonylation Process", the disclosure of which is incorporated herein by reference.

Figure 2:
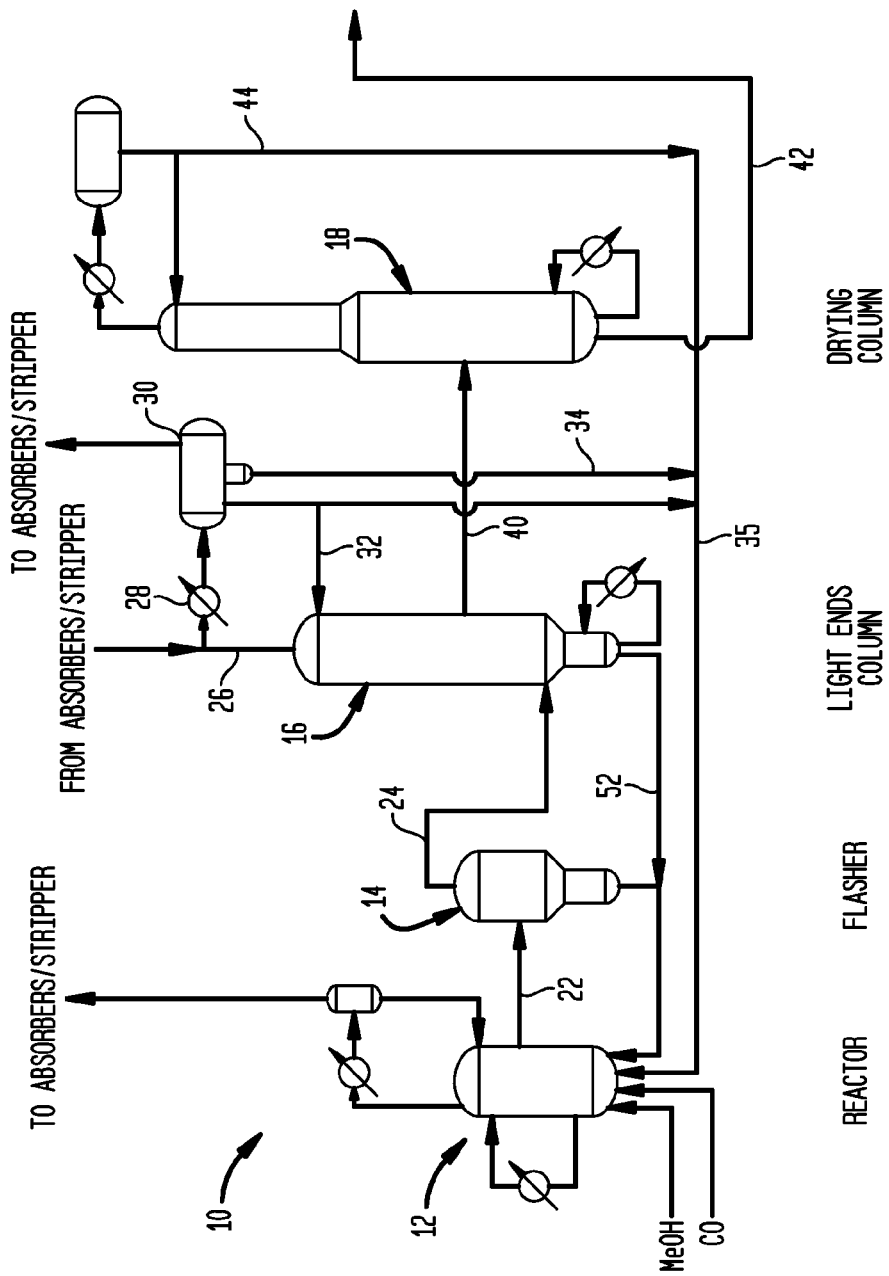
FIG. 2 is a schematic diagram of an apparatus suitable for practicing the process of the present invention.

Referring to FIG. 2, there is shown a carbonylation unit 10 of the class utilized in connection with the present invention. Unit 10 includes a reactor 12, a flasher 14, a light ends column 16, a drying or dehydration column 18 as well as optionally further purification, such as a heavy ends column to remove higher boiling impurities (not shown). Reactor 12 includes the reaction medium and there is fed thereto methanol and carbon monoxide. A portion of the reaction medium is continuously provided to flasher 14 via line 22 where crude product is flashed and sent to light ends column 16 via line 24 as a hot vapor feed.

In column 16, the product is purified of light components which exit the column via line 26, are condensed in a first condenser 28 and then decanted in a decanter 30. Conventionally, the light phase from decanter 30 is refluxed to column 16 via line 32, while the heavy phase from decanter 30 is returned to the reactor via lines 34, 35. Also provided, but not shown, are absorbers and strippers used to recycle material into the system.

A purified product stream 40 is withdrawn as a (preferably liquid) side stream from column 16 and fed to drying column 18 where water is removed from the partially purified product. Product is withdrawn via line 42. If necessary, further purification may be done. The overhead and some product acetic acid is used as reflux for column 18 or recycled to the reactor via line 44.

Column 16 generates a liquid residue stream 52 which is conventionally recycled with flasher residue to the reactor as shown.

EXAMPLES

Comparative Experiments

Utilizing a pilot scale apparatus simulating the reactor and flasher of the class described above in connection with FIG. 2, a lithium iodide promoted carbonylation system was operated for comparison with a system of the invention. Specifically, $Rh(OAc)_3$ (1000 ppm Rh) was introduced into a reactor such as reactor 12 with $AcOH/H_2O/HI$; the mixture was pressurized under 5 bar of CO at 140° C. during a 1 hour preformation step. The temperature was then increased in the reactor to 190° C. At that time methyl acetate, methyl iodide and the carbonylation catalyst precursor were introduced from a feed tank into the reactor. In a flash vessel such as that shown as flasher 14 of FIG. 2, a mixture of $H_2O/AcOMe/MeI/AcOH$ was heated to 140° C. When the temperature of the reactor reached 190° C. and the flasher reached 140° C., carbon monoxide and methanol were fed to the reactor along with recycled catalyst solution condensed from the base of the flasher, and the carbonylation reaction began. The flasher volume was replaced every 7.5 minutes at the circulation rates employed. Acetic acid product, water, methyl acetate and methyl iodide were condensed and collected from the flasher overhead. The continuous carbonylation process was operated for at least one hour. The reaction rate was determined by CO uptake measured in the reactor and by the amount of acetic acid collected in the vapor condensed flasher overhead material. The stability of the catalyst system was evaluated by measuring the amount of catalyst precipitation in the flasher base after the continuous operation was complete.

Further experimental details and results appear in Table 1 below and in FIG. 3.

TABLE 1

| Lithium Iodide Stabilized Methanol Carbonylation | |
|---|---|
| | Rh/LiI system Experiment 1 |
| Rh reactor concentration (ppm) | 989 |
| Lithium/rhodium reactor molar ratio | 77.1 |
| Lithium reactor concentration (ppm) | 5183 |
| Water reactor concentration (% wt) | 4.2 |
| Acetic Acid concentration (% wt) | 75.8 |
| Methyl iodide concentration (% wt) | 9.7 |
| Methyl Acetate concentration (% wt) | 1 |
| Methanol feed rate | 1.5 g/min |
| Reactor Temperature ° C.) | 190 |
| Flasher Temperature (° C.) | 142 |
| Time of the experiment (minutes) | 500 |
| Carbonylation Rate (CO), mol/L/hr | 17.3 |
| Carbonylation Rate (AcOH), mol/L/hr | 17.8 |
| Iodide reactor concentration (wt %) | 9.4 |
| Catalyst precursor used | $Rh(OAc)_3$, 5 wt % |
| Co catalyst precursor used | LiI |

Note: Two carbonylation rates, one determined by carbon monoxide uptake and one determined by quantified acetic acid product, are used to validate the results by similarity. A third carbonylation rate measuring MeOH consumed may also be used. The 989 ppm Rh concentration is comparable to 1000 ppm used in subsequent experiments. The 77.1 LiI molar ratio is comparable to the 76 ratio used in many subsequent experiments.

Figure 3:
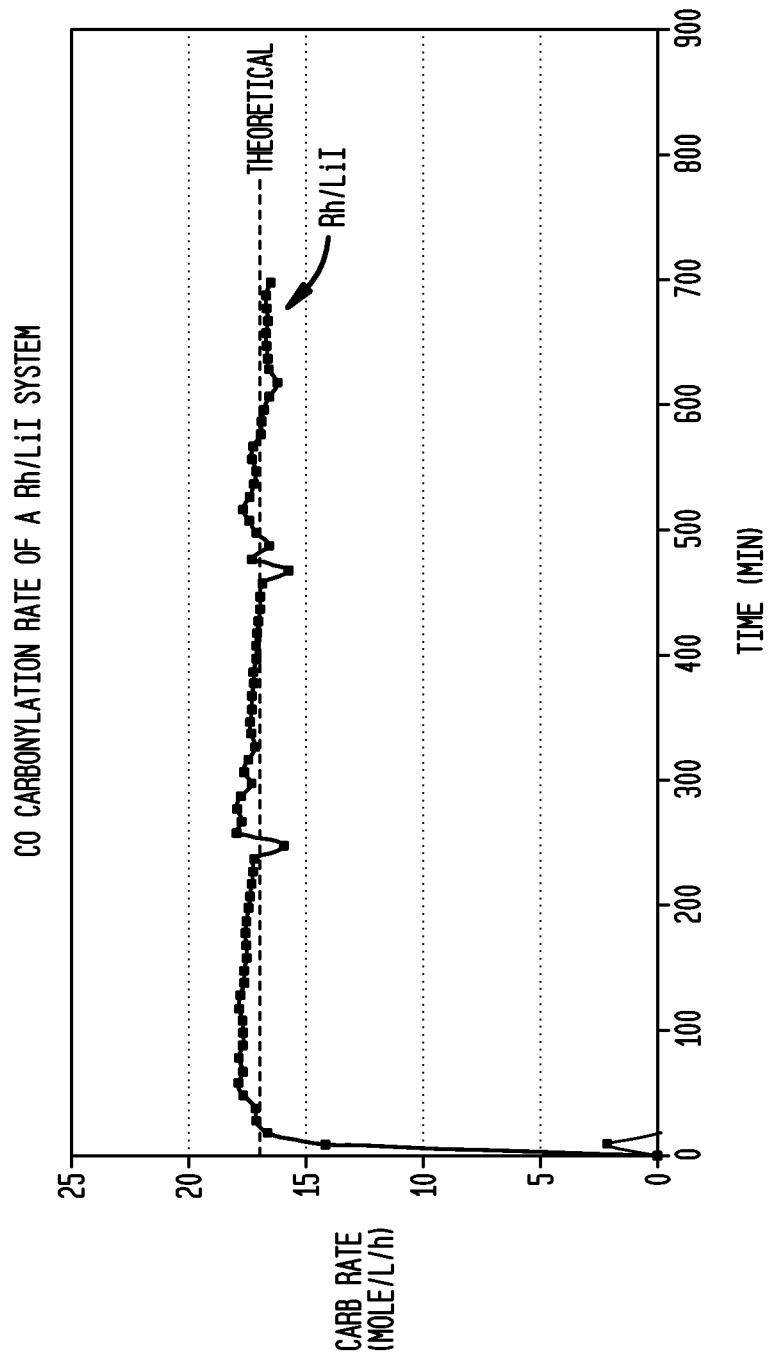
FIG. 3 is a plot of carbonylation rate versus time for a Rh/Li catalyst system.

It will be appreciated from Table 1 and FIG. 3 that under similar conditions, the chromium promoted system of the invention exhibited very similar performance to a lithium iodide stabilized and promoted system. Several advantages are noted, however, including the fact that the metallic promoter/rhodium molar ratios of the present invention may be substantially lower than lithium/rhodium molar ratios by a lithium iodide promoted system. Consequently, the inorganic iodide level is substantially lower in the chromium/rhodium system. This feature is believed to make it possible to run the process with less by-product generation than with conventional promoters.

We have found by titration of the reactor solution with silver nitrate that inorganic iodide levels are extremely low, i.e., 0.7-1.5 wt %, when using chromium as a rate promoter/catalyst stabilizer.

It is seen from the data in Table 1 that substituting a stabilizing and promoting metal for lithium iodide provides surprising stability and production rates (STY). Further examples demonstrate like results for other compositions of interest.

Example Series AA

Following generally the procedures noted above, further experiments were performed demonstrating an unstabilized rhodium system at a variety of water concentrations, and a lithium iodide-stabilized system at a variety of lithium iodide:rhodium molar ratios and water concentrations. In the examples below, except as otherwise noted, the conditions were as follows. Methyl iodide was added at a concentration of 10 wt %, and methyl acetate controlled at a concentration of 2%. Rhodium concentrations were 1000 ppm in the reactor. In each case, the balance of the reaction mixture at the start of the reaction was made up of acetic acid. Water concentrations ranged from 3 to 8%. With the exception of the rhodium tests without a co-catalyst, the metallic co-catalyst to rhodium molar ratio ranged from 0.5:1 to 115:1. The ratios provided are on a molar basis.

All the tests discussed immediately below were performed at reaction conditions of 190° C. and 30 bar total pressure. The methanol carbonylation reaction was allowed to proceed from about 2 hours to 9 hours.

Runs 2A-2C were operated using rhodium catalyst with no stabilizers (lithium iodide or other) added.

TABLE 2

Rhodium-catalyzed acetic acid production (no stabilizer or promoter present)

| Run | $H_2O$ (wt %) | Time run (hr) | STY (mol/l/hr) | Stability by visual observations |
|---|---|---|---|---|
| 2A | 8 | 3 | 10.5 | Unstable (small amounts of Rh precipitate into the flasher and the reactor) |
| 2B | 6 | 2 | 6.6 | Unstable (Precipitation of Rh into the flasher and the reactor) |
| 2C | 3 | 3 | 5.4 | Unstable (large amounts of Rh precipitate into the flasher and the reactor) |

Rh species were preformed from $Rh(OAc)_3$, at 10 wt % $H_2O$, 1 wt % HI and 89 wt % AcOH at 140° C. and 5 bar CO partial pressure for 1 hour. No stabilizer was introduced. Table 2 indicates that the methanol carbonylation reaction rate decreases with a decrease in reactor water concentration, which is well known to those skilled in the art. Also, in the absence of a rhodium catalyst stabilizer, rhodium precipitation increases as the water decreases.

TABLE 3

Acetic acid production co-catalyzed with lithium iodide.

| Run | Rh/LiI Ratio | $H_2O$ (wt %) | Time run (hr) | STY (mol/l/hr) | Stability by visual observations |
|---|---|---|---|---|---|
| 3A | 1/15 | 5 | 2.5 | 11.6 | Unstable (Precipitation of Rh into the flasher and the reactor) |
| 3B | 1/76 | 6 | 3 | 17.2 | Stable (No Rh precipitation) |
| 3C | 1/76 | 5 | 7 | 17.9 | Stable (No Rh precipitation) |
| 3D | 1/115 | 5 | 9 | 17.8 | Stable (No Rh precipitation) |

For experiments presented in Table 3, Rh species were preformed as described for Table 2. LiI was introduced in the flasher medium before this material was recycled to the reactor during the beginning of the experiment prior to methanol carbonylation. When the methanol carbonylation reaction began, the concentration of water in the reactor was about 9%. The concentration of water decreased to 5-6% after 1 hour and this water concentration was maintained through the remainder of the experiment.

Table 3 shows lithium iodide over a wide range of metal/Rh ratios and over a range of water concentrations. In sufficient amounts lithium iodide stabilizes rhodium effectively. Note that the reaction rate is influenced by the lithium iodide. These observations demonstrate the prior art of methanol carbonylation by rhodium promotion and stability by iodide salts.

Example Series B

We have found by titration of the reactor solution with silver nitrate that inorganic iodide levels are extremely low, i.e., as low as about 2 wt %, when using reduced lithium iodide concentrations supplemented with a metallic composition as a rate promoter/catalyst stabilizer.

With the exception of the rhodium tests without a co-catalyst, the lithium iodide to rhodium molar ratio ranged from 2 to 115. In most cases, a metallic co-catalyst was used at a metal to rhodium molar ratio ranging from 0.5 to 30. In a few cases, a second metallic co-catalyst component was used at a metal to rhodium molar ratio ranging from 1 to 20. The ratios provided are on a molar basis. The methanol carbonylation reaction was allowed to proceed from about 2 hours to 11.5 hours. Carbonylation rates ranged from 5.4 to 19 mol/L/hr.

It is seen from the data presented in the following Tables that supplementing low lithium iodide levels with a stabilizing and promoting metal provides surprising stability and production rates (STY). At water concentrations of up to 5%, chromium, vanadium, zinc, yttrium, and HPAs effectively stabilized the rhodium catalyst at reduced lithium iodide concentrations and provided good catalyst activity. Yttrium in combination with zinc also provided good catalyst stability and rate promotion. STY values were particularly high (e.g., greater than about 15) using chromium (Cr:LiI:Rh molar ratio of 20:15-30:1), vanadium (V:LiI:Rh molar ratio of 5:15:1), zinc acetate (Zn:LiI:Rh molar ratio of 1:15:1), yttrium (Y:LiI:Rh molar ratio of 15:10-30:1), and yttrium combined with zinc (Y:Zn:LiI:Rh molar ratio of 10:1:15:1).

Experiments with Lithium Iodide and a Single Metal

Following generally the procedures noted above, chromium, vanadium, yttrium, zinc, and so forth, were tested to determine their suitability as promoters and stabilizers. In the examples below, except as otherwise noted, the conditions were as follows. Methyl iodide was added at a concentration of 10 wt %, and methyl acetate controlled at a concentration of 2%. Rhodium concentrations were 1000 ppm in the reactor. In each case, the balance of the reaction mixture at the start of the reaction was made up of acetic acid. Water concentrations ranged from 2 to 6%. All the tests discussed below were performed at reaction conditions of 190° C. and 30 bar total pressure.

Tin was tested at a water concentration of 3% with conventional levels of lithium iodide, as shown in Table B4, below. As the Sn:Rh molar ratio increased, the STY fell, suggesting that the rhodium catalyst was increasingly stabilized to such an extent that it was less available to catalyze the reaction.

TABLE B4

Acetic acid production co-catalyzed with lithium iodide and tin.

| Run | Rh/LiI/Sn Ratio | $H_2O$ (wt %) | Co-catalyst | Time run (hr) | STY (mol/l/hr) | Stability by visual observations |
|---|---|---|---|---|---|---|
| B4A | 1/76/0.5 | 3 | LiI; $HSnI_3$ | 3 | 15.7 | Stable (No Rh precipitation) |
| B4B | 1/76/0.5 | 3 | LiI; $LiSnI_3$ | 3 | 17.4 | Stable (No Rh precipitation) |

TABLE B4-continued

Acetic acid production co-catalyzed with lithium iodide and tin.

| Run | Rh/LiI/Sn Ratio | $H_2O$ (wt %) | Co-catalyst | Time run (hr) | STY (mol/l/hr) | Stability by visual observations |
|---|---|---|---|---|---|---|
| B4C | 1/76/1 | 3 | LiI;$SnI_4$ | 3 | 15.8 | Stable (No Rh precipitation, but Sn at the top of the flasher) |
| B4D | 1/76/5 | 3 | LiI; $Sn(OAc)_2$ | 3 | 13.6 | Stable (No Rh precipitation but Sn at the top of the flasher) |

$HSnI_3$ was prepared from $SnI_2$ or from $Sn(OAc)_2$ with HI/LiI (3/1 molar ratio of LiI/Sn)/$H_2O$/AcOH at 60° C. $LiSnI_3$ was prepared with HI/AcOH/$H_2O$ and a large amount of LiI (20/1 molar ratio of LiI/Sn) at 140° C. $SnI_4$ was introduced in solution with MeI and AcOMe. The resulting co-catalyst solution was introduced into the reactor through a feed tank after preformation of active Rh species.

The difference between the first and second runs lies in the co-catalyst's preformation, which allows a difference in stability of Rh. The second run (Rh/LiI/Sn molar ratio of 1/76/0.5) has carbonylation rates the same as does the low water run for Rh/LiI alone (1/76 molar ratio, 3 wt % water).

As the concentration of Sn was increased, Rh stability remained strong. However, the production rate decreased. Volatility of tin (loss of solubility) was considered responsible for this result. If tin concentrations are kept below the solubility limit, tin acts as a good stabilizer. Sn is considered primarily a stabilizer because an increase in the molar ratio of Sn results in a decrease of the STY.

It is seen from the data in the following tables that reduced lithium iodide levels in conjunction with the presence of certain stabilizing or promoting metals provides surprising stability and production rates (STY).

TABLE B5

Acetic acid production co-catalyzed with lithium iodide and zinc.

| Run | Rh/LiI/Zn Ratio | $H_2O$ (wt %) | Co-catalyst | Time run (hr) | STY (mol/l/hr) | Stability by visual observations |
|---|---|---|---|---|---|---|
| B5A | 1/76/1 | 5 | LiI; $Zn(OAc)_2 \cdot 2H_2O$ | 5.5 | 17.6 | Stable (No Rh, No Zn precipitations) |
| B5B | 1/15/1 | 5 | LiI; $Zn(OAc)_2 \cdot 2H_2O$ | 3.5 | 17 | Stable (No Rh, No Zn precipitations) |
| B5C | 1/15/1 | 5 | LiI; $ZnI_2$ | 8 | 14.8 | Stable (No Rh, No Zn precipitations) |

When preformation of the active Rh species in the reactor was finished, the co-catalyst was introduced through a feed tank into the reactor. $Zn(OAc)_2 \cdot 2H_2O$ was introduced in water solution, whereas $ZnI_2$ was introduced in AcOH solution. At this initial time of the experiment, the concentration of water in the reactor was about 9%. LiI was introduced in the flasher medium before this material was recycled to the reactor during the beginning of the experiment and prior to methanol carbonylation. The methanol carbonylation reaction then began. During the run, the concentration of water decreased to 5-6% after 1 hour and this water concentration was maintained through the remainder of the experiment. During this time Rh—Zn complexes were forming.

The first run (Rh/LiI/Zn molar ratio of 1/76/1) has similar carbonylation rates to that of Rh/LiI (1/76 molar ratio, 5 wt % water) alone.

Comparing tests of rhodium catalyst systems with Rh/LiI no co-catalyst metal and with Rh/LiI/Zn at the same concentration of LiI (both at a Rh/LiI molar ratio of 1/15), Rh/LiI/Zn was a more stable and more active system. Note that zinc acetate performed better than zinc iodide. Therefore, addition of zinc allows the reduced application of lithium iodide.

There was a loss of activity when the experiment was stopped at night.

TABLE B6

Acetic acid production co-catalyzed with lithium iodide and yttrium.

| Run | Rh/LiI/Y Ratio | $H_2O$ (wt %) | Co-catalyst | Time run (hr) | STY (mol/l/hr) | Stability by visual observations |
|---|---|---|---|---|---|---|
| B6A | 1/2/13 | 5 | LiI; $Y(OAc)_3 \cdot H_2O$ | 2.7 | / | Unstable (Rh precipitation) |
| B6B | 1/4/13 | 5 | LiI; $Y(OAc)_3 \cdot H_2O$ | 3 | / | Unstable (Rh precipitation) |
| B6C | 1/30/15 | 5 | LiI; $Y(OAc)_3 \cdot H_2O$ | 11.5 | 17.7 | Stable (No Rh, No Y precipitations) |
| B6D | 1/76/30 | 5 | LiI; $Y(OAc)_3 \cdot H_2O$ | 2.5 | 18.3 | Unstable (solubility concerns of Y) |
| B6E | 1/76/20 | 5 | LiI; $Y(OAc)_3 \cdot H_2O$ | 9 | 18.7 | Stable (No Rh, No Y precipitations, No solubility concerns) |
| B6F | 1/115/20 | 5 | LiI; $Y(OAc)_3 \cdot H_2O$ | 14 | 19 | Stable (No Rh, No Y precipitations, No solubility concerns) |
| B6G | 1/10/15 | 5 | LiI; $Y(OAc)_3 \cdot H_2O$ | 6.5 | 16 | Stable (No Rh, No Y precipitations, No solubility concerns) |
| B6H | 1/15/15 | 5 | LiI; $Y(OAc)_3 \cdot H_2O$ | 6 | 16 | Stable (No Rh, No Y precipitations, No solubility concerns) |

When the preformation of the active Rh species in the reactor was finished, $Y(OAc)_3$ was introduced directly into the reactor (after cooling and depressurizing the reactor). The reactor was then heated. At this time (with the addition of Y salts in water), the concentration of water in the reactor was about 20%, depending upon the concentration of Y salts which ranged from a Y/Rh molar ratio of from 13 to 30. Then LiI was introduced into the flasher and the methanol carbonylation reaction began. The concentration of water decreased (to 5-6%) after 2 hours and this water concentration was maintained through the remainder of the experiment. During this time Rh—Y complexes were forming.

At very low concentrations of LiI (molar ratios of 1/2/13 and 1/4/13), Rh was not stabilized by yttrium. However, at relatively low concentrations of LiI (Rh/LiI molar ratio of 1/15), Y stabilizes and increases the activity of the system compared to Rh/LiI alone.

Y increases the activity of the system in both the fifth run of the above table (1/76/20 molar ratio) compared to the Rh/LiI test (1/76 molar ratio, 5 wt % water), while maintaining stability. Y is a good co-catalyst in terms of activity, but has solubility concerns in the medium allowing the non-stability of Rh.

In both the run using Rh/LiI alone (1/76 molar ratio, 5 wt. % water) and the run in Table B6 with a Rh/LiI/Y molar ratio of 1/30/15, stability was maintained, and the carbonylation rate was the same. Therefore, yttrium allows the reduction of LiI application. Comparing tests of Rh/LiI/Y at molar ratios of 1/10/15 and 1/15/15, the same carbonylation rate was achieved. Therefore, a lower concentration of LiI can be used in this system.

It is noted that a large concentration of LiI (a Rh/LiI molar ratio of 1/115) slightly increases the activity of the system.

Combinations of lithium iodide and yttrium are also believed suitable for use with water concentrations of 5 wt % or below in lithium iodide amounts of 15 to 76 times the amount of rhodium present on a molar basis, and yttrium amounts of 15 to 20 times the amount of rhodium present on a molar basis.

TABLE B7

Acetic acid production co-catalyzed with lithium iodide and HPA.

| Run | Rh/ LiI/HPA Ratio | $H_2O$ (wt %) | Co-catalyst | Time run (hr) | STY (mol/ l/hr) | Stability by visual observations |
|---|---|---|---|---|---|---|
| B7A | 1/15/5 | 5 | LiI; $H_3PW_{12}O_{40} \cdot xH_2O$ | 3 | 14.3 | Stable (No Rh precipitation) |
| B7B | 1/15/7.5 | 5 | LiI; $H_3PW_{12}O_{40} \cdot xH_2O$ | 2 | 12 | Stable (No Rh precipitation) |

When the preformation of Rh species in the reactor was finished, HPA was introduced in AcOH solution through a feed tank into the reactor. At this time, the concentration of water in the reactor was about 9%. LiI was introduced in the flasher medium before this material was recycled to the reactor during the beginning of the experiment and prior to methanol carbonylation. The methanol carbonylation reaction then began. The concentration of water decreased to 5-6% after 1 hour and this water concentration was maintained through the remainder of the experiment. During this time Rh-HPA complexes were forming.

Comparing tests of rhodium/lithium iodide catalyst systems with and without HPA (at a Rh/LiI molar ratio of 1/15), it is noted that HPA stabilizes Rh. Therefore, addition of HPA allows the reduced application of lithium iodide. However, as the concentration of HPA increases, the activity of the system decreases.

Combinations of lithium iodide and heteropoly acids are also believed suitable for use with water concentrations of 5 wt % or below in lithium amounts of 15 to 30 times the amount of rhodium present on a molar basis and a heteropoly acid in amounts of 2 to 5 times the amount of rhodium present on a molar basis.

TABLE B8

Acetic acid production co-catalyzed with lithium iodide and chromium.

| Run | Rh/ LiI/Cr Ratio | $H_2O$ (wt %) | Co-catalyst | Time run (hr) | STY (mol/ l/hr) | Stability by visual observations |
|---|---|---|---|---|---|---|
| B8A | 1/30/20 | 5 | $CrCl_3 \cdot 6H_2O$; LiI | 10 | 17 | Stable (No Rh precipitation) |

Combinations of lithium iodide and chromium are also believed suitable for use with water concentrations of 5 wt % or below using lithium iodide amounts of 10 to 15 times the amount of rhodium present on a molar basis and chromium amounts of 10 to 20 times the amount of rhodium present on a molar basis.

Experiments with Lithium Iodide and a Binary Metal Co-Catalyst

In the examples below, except as otherwise noted, the conditions were as follows. Methyl iodide was added at a concentration of 10 wt %, and methyl acetate controlled at a concentration of 2%. Rhodium concentrations were 1000 ppm in the reactor. In each case, the balance of the reaction mixture at the start of the reaction was made up of acetic acid. Water concentrations ranged from 2 to 6%. All the tests discussed below were performed at reaction conditions of 190° C. and 30 bar total pressure.

TABLE B9

Acetic acid production co-catalyzed with lithium iodide, yttrium, and zinc.

| Run | Rh/LiI/ Y/Zn Ratio | $H_2O$ (wt %) | Co-catalyst | Time run (hr) | STY (mol/ l/hr) | Stability by visual observations |
|---|---|---|---|---|---|---|
| B9A | 1/15/10/1 | 5 | LiI, $Y(OAc)_3 \cdot H_2O$; $Zn(OAc)_2 \cdot 2H_2O$ | 2 | 18.5 | Stable (No Rh, No Y precipitations, No solubility concerns of Y) |

When the preformation of Rh species in the reactor was finished, $Zn(OAc)_2.2H_2O$ was introduced in water solution through a feed tank into the reactor. Then the reactor was cooled and depressurized and $Y(OAc)_3$ was introduced into the reactor. At this initial time of the experiment, the concentration of water in the reactor was about 15%. LiI was in the flasher medium before this material was recycled to the reactor during the beginning of the experiment and prior to methanol carbonylation. The reactor was then heated and the reaction began. The concentration of water decreased to 5-6% after 2 hours and this water concentration was maintained through the remainder of the experiment. During this time Rh—Zn and Rh—Y complexes were forming.

The addition of Y/Zn to Rh/LiI with a Rh/LiI molar ratio of 1/15 increases the stability and the activity of the system compared to Rh/LiI alone. Therefore, addition of yttrium and zinc allows the reduced application of lithium iodide. The combination of yttrium and zinc is more effective as a rate promoter than either component alone.

Combinations of lithium iodide, yttrium, and zinc are also believed suitable for use with water concentrations of 5 wt % or below in lithium iodide amounts of about 15 times the amount of rhodium present, yttrium amounts of about 5 to 10 times the amount of rhodium present, and zinc amounts of about 3 to 10 times the amount of rhodium present, on a molar basis. Similarly, combinations of lithium iodide with yttrium and chromium or a heteropoly acid are believed suitable for use with water concentrations of 5 wt % or below. Suitable amounts include lithium iodide amounts about 10 to 15 times the amount of rhodium present, chromium amounts 10 to 20 times the amount of rhodium present, and yttrium in amounts of 5 to 10 times the amount of rhodium present on a molar basis. Suitable amounts include lithium iodide amounts of about 10 to 15 times the amount of rhodium present, yttrium amounts of about 10 times the amount of rhodium present, and HPA amounts of 1 to 5 times the amount of rhodium present, on a molar basis.

Example B10

End-Run Analyses

To demonstrate that selected co-catalyst metals contribute substantially less than equivalent amounts of inorganic iodide to a carbonylation system at equilibrium, a series of runs were performed under continuous conditions following generally the procedures noted above. For comparison, a run co-catalyzed with lithium iodide alone was performed as described generally above.

In the examples below, except as otherwise noted, the conditions were as follows. Methyl iodide was added at a concentration of 10 wt %, and methyl acetate controlled at a concentration of 2%. Rhodium concentrations were 1000 ppm in the reactor. The balance of the reaction mixture at the start of the reaction was made up of acetic acid. All the tests discussed below were performed at reaction conditions of 190° C. and 30 bar total pressure.

Although most of the examples provided were operated at a water concentration of 5%, two examples were also provided at a water concentration of 2%. These examples demonstrate the applicability of the invention to carbonylation in low water conditions. The conditions and results are summarized in Tables B10 and B11, below. Table B10 provides data comparable to the data provided in the previous examples. Table B11 provides additional information not available for the previous examples.

Note that all of the co-catalytic transition metal runs achieved production rates comparable to the lithium iodide run and provided catalyst stability to the system. A sample of the reaction mixture from each run was titrated for halide (e.g., iodide) content. Corrosion metal content and resultant impurities were also determined. The results are shown below.

For instance, for Example B10D, chromium was introduced through a feed tank into the reactor after the preformation of the active Rh species in the reactor at the beginning of the reaction. At this time, the concentration of water in the reactor was about 18%. LiI was introduced in the flasher medium before this material was recycled to the reactor during the beginning of the experiment and prior to methanol carbonylation. Then the methanol carbonylation reaction began and the concentration of water decreased to about 5% after 2 hours and this water concentration was maintained through the remainder of the experiment. During this time Rh—Cr complexes were forming.

Experiments were performed using LiI/Fe (15/25 molar ratio) and LiI/Ni (15/15 molar ratio). However, in both cases, the solubility of the cocatalyst was unstable. Therefore, these runs were not evaluated further, and are not discussed in Tables B10 and B11.

TABLE B10

Acetic acid production co-catalyzed with metallic co-catalysts.

| Run | Rh/LiI/Metal Ratio | Co-catalyst | Cocatalyst Concentration (wt %) | $H_2O$ (wt %) | Time run (hr) | STY (mol/l/hr) | Stability by visual observations |
|---|---|---|---|---|---|---|---|
| B10A | 1/76 | LiI | Li: 0.5 | 5 | 4 | 18 | Stable |
| B10B | 1/15/1 | LiI; $Zn(OAc)_2$ | Li: 0.1; Zn: 0.06 | 5 | 4 | 16 | Stable |
| B10C | 1/15/5 | LiI; $VCl_3$ | Li: 0.1; V: 0.25 | 5 | 3 | 16 | Stable |
| B10D | 1/15/15 | LiI; $Y(OAc)_3$ | Li: 0.1; Y: 1.3 | 5 | 4 | 16 | Stable |
| B10E | 1/15/20 | LiI; $Cr(OAc)_3$ | Li: 0.1; Cr: 1 | 5 | 4 | 16 | Stable |
| B10F | 1/38 | LiI | Li: 0.25 | 5 | 4 | 15.5 | Unstable |
| B10G | 1/76 | LiI | Li: 0.5 | 2 | 4 | 16.5 | Stable |
| B10H | 1/15/20 | LiI; $Cr(OAc)_3$ | Li: 0.1; Cr: 1 | 2 | 4 | 16 | Stable |

TABLE B11

Iodide concentration, end-run conditions, and impurities analysis for various cocatalysts.

| Run | Theoretical Iodide Content (wt %) | Iodide titration results (wt %) | End Run conditions | | | Impurities, ppm | | | |
|---|---|---|---|---|---|---|---|---|---|
| | | | $H_2O$ (wt %) | AcOMe (wt %) | MeI (wt %) | Acetaldehyde | Crotonaldehyde | Ethylcrotonaldehyde | Propionic Acid |
| B10A | 9.1 | 9 | 4 | 1 | 10 | 457 | ND | ND | 166 |
| B10B | 2 | 2.1[1] | 6 | 2 | 11 | 247 | ND | ND | 90 |
| B10C | 3.6 | 2.5 | 4 | 2 | 9 | 272 | ND | ND | 79 |
| B10D | 7.3 | 3.5 | 5 | 6 | 11 | 214 | ND | ND | 36 |
| B10E | 9.1 | 3.1 | 4 | 2 | 13 | 149 | ND | ND | 15 |
| B10F | 4.6 | 5[1] | 5 | 4 | 16 | 256 | ND | ND | 52 |
| B10G | 9.1 | 8 | 2.1 | 2.5 | 9.1 | 297 | ND | ND | 246 |
| B10H | 9.1 | 3.6 | 2.9 | 5.6 | 10.5 | 114 | ND | ND | 169 |

[1]Difference between calculated theoretical and experimentally measured iodide results is believed due to experimental error; For purposes of analysis, the measured iodide value of Li and Zn (Run B10B) has been rounded to 2, and the theoretical iodide value of Li at an Rh/Li molar ratio of 1/38 (Run B10F) has been rounded to 5.

Theoretically equivalent inorganic iodide content was calculated as follows. Iodine has a molecular weight of 126.904 g/mol. The theoretical mass of inorganic iodide was calculated by multiplying the molar ratio of metal to rhodium by the valence of the metal and the molecular weight of iodine. The mass of inorganic iodide was divided by the total mass of the reaction mixture and multiplied by 100 to achieve a theoretical weight percent inorganic iodide content. For example, given a rhodium concentration of 1000 ppm, a chromium form of $Cr(OAc)_3$ (i.e., valence of 3), and a chromium:rhodium molar ratio of 20:1, the theoretical inorganic iodide content in Run B16E (Chromium) was calculated as follows.

Mass of Inorganic Iodide:

20 mol×valence 3×126.904 g I/mol=7614.24 g (based on one mol of Rh)

Total Reaction Mixture Mass (Based on one mol of Rh): Rh: 102.905 g

Total mass: 1000×mass of Rh: 1000×102.905 g=102905 g

Theoretical Inorganic Iodide Content:

(7614.24 g/102905 g)×100=7.3 wt %

Alternatively, given the mass of chromium in weight %, the theoretical iodide content may be found by multiplying the mass of chromium by the valence and a ratio of the molecular weight of iodine to the molecular weight of chromium. A theoretical inorganic iodide value was similarly calculated for the lithium iodide present in the system, and the theoretical values of iodide from chromium and iodide from lithium were added. Note that the calculations provided herein use the valence of the form of each metallic co-catalyst as it was introduced. An alternate valence would only be used if it was otherwise clear that the valence of the metal changes after introduction to the system.

Additional analysis showed that the reaction mixture of Example B10A contained corrosion metals in the following concentrations: 20 ppm of iron; 186 ppm of nickel; and 163 ppm of molybdenum. The quantity of corrosion metals is a function of corrosion of the reactor material. The amount varies depending on a variety of factors: run time, temperature, catalysts used and the pre-existing corrosion level of the reactor. Thus, it is difficult to compare corrosion metal amounts between runs, or to compare corrosion metal amounts from one system to another.

The actual iodide content in the system was determined by titration as described above. Note that entries labeled "ND" indicate that the impurity was not detected. The detection limit for the analytical method used herein is 10 ppm.

Without intending to be bound by theory, the propionic acid levels are believed to be more representative of the impurity profile achieved by each composition than is acetaldehyde. Acetaldehyde has a boiling point of about 20.2° C., in contrast to propionic acid which has a boiling point of about 140.7° C. Acetaldehyde and propionic acid flash off with the product acetic acid (B.P. 118° C.) and are condensed. A fraction of the acetaldehyde may be lost as the condensed mixture is removed from the condenser as well as during analysis of the impurities.

The results in Table B11, See also FIG. 4 and FIG. 5, show that metallic co-catalyst compositions including metals such as chromium and lanthanum and binary metal co-catalyst compositions such as yttrium and zinc achieve comparable results to a rhodium/lithium iodide carbonylation system in terms of STY and catalyst stability, but contribute a significantly lower inorganic iodide concentration to the reaction mixture. Further, the impurity profile, i.e., the relative amounts of each impurity, is profoundly affected by the metal in each run. When the inorganic iodide of the system is low, such impurities are dramatically reduced. Iodide levels below about 1 weight % reduced acetaldehyde levels by about 48%, and propionic acid levels by about 78%, compared to the lithium iodide system results. Run B16H demonstrates that the method according to the invention can be successfully performed at low water concentrations. Without being bound by theory, it is believed that the level of acetaldehyde decreases with decreasing water concentration because there is less hydrogen available in the reaction medium.

Make rates for impurities produced in a system according to the invention may be calculated by multiplying the impurity concentration (ppm) in the acetic acid product by the carbonylation rate, or STY (mol/L/hr), multiplied by the molecular weight of acetic acid (60.05196 g/mol), divided by the molecular weight of the impurity, resulting in a rate of moles impurity per liter per hour ($\times 10^{-6}$). For propionic acid, the molecular weight is 74.07854 g/mol; for acetaldehyde, the molecular weight is 44.05256. The metallic co-catalysts according to the invention have been shown to achieve propionic acid make rates about 33% to about 92% lower than a conventional lithium iodide-stabilized system, and acetaldehyde make rates about 36% to about 71% lower than a conventional system.

While the metals exemplified above are preferred, other metals may also be used, as discussed below. As a result primarily of the experimentation described above, manganese, zinc, ruthenium, indium, heteropoly acids, and tin are considered to be primarily stabilizers. Vanadium, barium, and yttrium are considered to be primarily activators. Chromium, nickel, strontium, and lanthanum are considered to be both activators and stabilizers. Beryllium, cobalt, copper, hafnium, and platinum may be successful activators or stabilizers. Several metals showed promising results during testing, but were introduced in a form that did not achieve adequate solubility. A soluble form of these metals may also provide activation and/or stabilization. These metals include aluminum, titanium, iron, zirconium, molybdenum, tungsten, and bismuth.

Other combinations believed suitable for use in systems having a water concentration of 5 wt % or less are listed in Table B12.

TABLE B12

Acetic acid production co-catalyzed with lithium iodide and various metals.

| Run | Co-catalyst | Rh/LiI/Metal Ratio |
|---|---|---|
| B12A | LiI/Be | 1/15/25 |
| B12B | LiI/Co | 1/15/25 |
| B12C | LiI/Hf | 1/15/25 |
| B12D | LiI/Mn | 1/15/25 |
| B12E | LiI/Mo | 1/15/15 |
| B12F | LiI/Pt | 1/15/25 |
| B12G | LiI/Sr | 1/15/25 |
| B12H | LiI/Ti | 1/15/5 |
| B12I | LiI/Zr | 1/15/25 |

There is thus provided in one aspect of the invention, a process utilizing an iodide salt and a metallic co-catalyst together with rhodium metal catalyst. A continuous process for the production of acetic acid comprises reacting a compound selected from the group consisting of methanol and reactive derivatives thereof, with carbon monoxide to produce acetic acid in an aqueous reaction mixture, the reaction being carried out while maintaining a concentration of water in the reaction mixture of from 0.1 wt % up to about 8 wt %, the reaction also being carried out in the presence of a homogeneous rhodium-based catalyst system comprising: (i) a rhodium catalyst metal; (ii) an iodide promoter; (iii) an inorganic iodide-providing co-catalyst at a molar ratio of inorganic iodide-providing co-catalyst:Rh of less than 76:1; and (iv) a metallic co-stabilizing or rate-promoting composition including a metal selected from the group consisting of transition metals, indium, strontium, barium, zinc, tin, HPA, and mixtures thereof; and (b) recovering acetic acid from the reaction mixture. The process is controlled and the metallic co-stabilizing or rate-promoting composition is selected so that it is effective as a stabilizer or a rate promoter, and the reaction mixture contains substantially less than a theoretically equivalent inorganic iodide content corresponding to the presence of the metallic co-stabilizing or rate-promoting composition and the inorganic iodide-providing co-catalyst. The process is operated wherein the amount of inorganic iodide present is less than 70% of the theoretically equivalent inorganic iodide content or wherein the amount of inorganic iodide present is less than 50% of the theoretically equivalent inorganic iodide content or wherein the amount of inorganic iodide present is less than 40% of the theoretically equivalent inorganic iodide content such as wherein the amount of inorganic iodide present is less than 35% of the theoretically equivalent inorganic iodide content. Likewise, the process is operated with a total inorganic iodide content in the reaction mixture of less than 5 weight % or less than 4 weight %. In some cases the process is operated with a total inorganic iodide content in the reaction mixture of less than 3.5 weight % or less than 3 weight % or less than 2.5 weight %. The percentage values of inorganic iodide as characterized by theoretically equivalent inorganic iodide content corresponding to the presence of the metallic co-stabilizing or rate-promoting composition and weight percent values noted above may be independently combined in the various embodiments of the invention. The inorganic iodide-providing co-catalyst is present in an amount of less than 50 times the amount of rhodium on a molar basis such as in an amount of less than 40 times the amount of rhodium on a molar basis or less than 25 times the amount of rhodium on a molar basis.

In a preferred embodiment of this class, the inorganic iodide-providing co-catalyst is lithium iodide present in a lithium iodide:rhodium molar ratio of about 1:1 up to a ratio of about 50:1 such as wherein the inorganic iodide-providing co-catalyst is lithium iodide present in a lithium iodide:rhodium molar ratio of about 5:1 up to a ratio of about 35:1.

In general, the catalytic process of the invention utilizing iodide salts is further characterized by a STY greater than 10 moles/L/hr. In its various aspects, the iodide promoter is methyl iodide and the water content of the reaction mixture is maintained at less than 7 weight %. In some cases, the water content of the reaction mixture is maintained at a level of from 1 weight % to 7 weight % such as from 2 weight % to 6 weight % or the water content of the reaction mixture may be maintained at a level of from 0.2 weight % to 5 weight %; including at a level of from 3 weight % to 5 weight % or wherein the water content of the reaction mixture is maintained at less than 3 weight %. Alternative embodiments are wherein the water content of the reaction mixture is maintained at a level of from 0.5 weight % to 3 weight %; or from 1 weight % to 2.75 weight %; or from 1.5 weight % to 2.5 weight % and the process is operated with a total inorganic iodide content in the reaction mixture of less than 4.5 weight % and the water content of the reaction mixture is maintained at a level of less than or equal to 5 weight %. Total inorganic iodide content in the reaction mixture of less than 4 weight % and the water content of the reaction mixture is maintained at a level of less than 5 weight %. The process is typically operated with a total inorganic iodide content in the reaction mixture of less than 3.5 weight % and the water content of the reaction mixture is maintained at a level of less than 5 weight % such as wherein the process is operated with a total inorganic iodide content in the reaction mixture of less than 3 weight % and the water content of the reaction mixture is maintained at a level of less than 5 weight %. The process may be operated with a total inorganic iodide content in the reaction mixture of less than 2.5 weight % and the water content of the reaction mixture is maintained at a level of less than 5 weight % or wherein the total inorganic iodide content in the reaction mixture of less than 2.5 weight % and the water content of the reaction mixture is maintained at a level of from 0.5 to less than 5 weight %. The metallic co-stabilizing or rate-promoting composition may comprise a single metal compound and the metallic co-stabilizing or rate-promoting composition may be present in an amount of from 0.5 times to about 10 times the amount of rhodium on a molar basis such as wherein the metallic co-stabilizing or rate-promoting composition is present in an amount of at least 5 times the amount of rhodium on a molar basis or wherein the metallic co-stabilizing or rate-promoting composition is present in an amount of at least 10 times the amount of rhodium on a molar basis. In some preferred cases, the metallic co-stabilizing or rate-promoting composition comprises chromium present in a chromium:rhodium molar ratio of about 5:1 up to less than 30:1. Particular embodiments include those wherein the metallic co-stabilizing or rate-promoting composition comprises yttrium present in an yttrium:rhodium molar ratio of about 5:1 to less than 30:1 or wherein the metallic co-stabilizing or rate-promoting composition comprises vanadium in a vanadium:rhodium molar ratio of about 0.5:1 and up to 10:1. Other species of the invention are wherein the metallic co-stabilizing or rate-promoting composition comprises zinc in a zinc:rhodium molar ratio of about 1:1 and up to about 10:1 and wherein the metallic co-stabilizing or rate-promoting composition comprises a heteropoly acid in a heteropoly acid:rhodium molar ratio of about 0.5:1 and up to about 10:1 or wherein the metallic co-stabilizing or rate-promoting composition comprises two metal components. The two metal compounds may comprise yttrium and zinc wherein yttrium is present in a yttrium:rhodium molar ratio of about 5:1 to less than 20:1, and zinc is present in a zinc:rhodium molar ratio of about 0.5:1 up to 10:1.

The catalytic process of the invention utilizing iodide salts may be operated wherein the reaction mixture contains from 250 ppm rhodium to 3000 ppm rhodium such as wherein the reaction mixture contains from 500 ppm rhodium to 2000 ppm rhodium.

Typically, the metal composition is added to the reaction mixture in the +1, +2, +3, +4, +5, or +6 oxidation state.

The molar ratio of metal/rhodium in the reaction mixture is suitably at least 0.5/1 in many implementations of the inventive process.

Another particularly useful commercial embodiment is a continuous process for the production of acetic acid comprising: (a) reacting a compound selected from the group consisting of methanol and reactive derivatives thereof, with carbon monoxide to produce acetic acid in an aqueous reaction mixture disposed in a pressurized reactor, the reaction being carried out in the presence of a homogeneous rhodium-based aqueous catalyst system comprising: (i) a rhodium catalyst metal; (ii) methyl iodide maintained in said reaction mixture in a concentration of from about 1 to about 20 weight percent; (iii) a lithium iodide cocatalyst at a molar ratio of LiI:Rh of less than 76:1; and (iv) a metallic co-stabilizing or rate-promoting composition selected from the group consisting of transition metals, zinc, tin, a heteropoly acid, indium, strontium, barium, and mixtures thereof; (v) water maintained in said reaction mixture in a concentration of from 0.1 weight percent up to less than 8 weight percent; (vi) methyl acetate maintained in said reaction mixture in a concentration of from about 0.5 to about 30 weight percent; and (vii) acetic acid; (b) providing a stream of the reaction mixture to a flash vessel; (c) flashing crude acetic acid product from the reaction mixture to generate a crude product stream including acetic acid, methyl acetate, methyl iodide and water; and (d) purifying the crude product stream to remove methyl acetate, methyl iodide and water therefrom, to obtain a purified acetic acid product, wherein the process is controlled and the metallic co-stabilizing or rate-promoting composition is selected so that the metallic co-stabilizing or rate-promoting composition is effective as a stabilizer or a rate promoter, and the reaction mixture contains substantially less than a theoretically equivalent inorganic iodide content corresponding to the presence of the metallic co-stabilizing or rate-promoting composition and the lithium iodide co-catalyst. This process also has the features and components in the amounts recited above and is preferably further characterized by a propionic acid concentration of less than 30 parts per million as measured at the flash vessel overhead. A partial pressure of carbon monoxide may be maintained above 1 bar in the pressurized reactor and/or wherein a partial pressure of carbon monoxide may be maintained below 1 bar in the flash vessel.

Another process of the invention is a continuous process for the production of acetic acid comprising: (a) reacting a compound, selected from the group consisting of methanol and reactive derivatives thereof, with carbon monoxide to produce acetic acid in an aqueous reaction mixture, the reaction being carried out while maintaining a concentration of water in the reaction mixture of from 0.1 wt % up to about 5 wt %, the reaction also being carried out in the presence of a homogeneous rhodium-based catalyst system comprising: (i) a rhodium catalyst metal; (ii) an iodide promoter; and (iii) an inorganic iodide-providing co-catalyst at a molar ratio of inorganic iodide-providing co-catalyst:Rh of less than 70:1; and (iv) a metallic co-stabilizing or rate-promoting composition including a metal selected from the group consisting of transition metals, indium, strontium, barium, zinc, tin, HPA, and mixtures thereof, in a metal to rhodium molar ratio of at least 0.5:1 and up to 20:1; and (b) recovering acetic acid from the reaction mixture, wherein the process is controlled and the metallic co-catalyst composition is selected so that it is effective as a stabilizer or a rate promoter.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A continuous process for the production of acetic acid comprising:
   (a) reacting a compound, selected from the group consisting of methanol and reactive derivatives thereof, with carbon monoxide to produce acetic acid in an aqueous reaction mixture, the reaction being carried out while maintaining a concentration of water in the reaction mixture of from 0.1 wt % up to about 8 wt %, the reaction also being carried out in the presence of a homogeneous rhodium-based catalyst system comprising:
   (i) a rhodium catalyst metal;
   (ii) an iodide promoter;
   (iii) an inorganic iodide-providing co-catalyst at a molar ratio of inorganic iodide-providing co-catalyst:Rh of less than 76:1; and
   (iv) a metallic co-stabilizing or rate-promoting composition including a metal selected from the group consisting of transition metals, indium, strontium, barium, zinc, tin, HPA, and mixtures thereof; and
   (b) recovering acetic acid from the reaction mixture;
   wherein the inorganic iodide-providing co-catalyst and the metal of the metallic co-stabilizing or rate-promoting composition are present in a molar ratio of 15:1 to 0.6:1 and wherein further the reaction mixture contains less than 70% of a theoretical amount of inorganic iodide equivalent to the presence of both the metal of the metallic co-stabilizing or rate-promoting composition and the inorganic iodide-providing co-catalyst.

2. The process according to claim 1, wherein the process is operated with a total inorganic iodide content in the reaction mixture of less than 5 weight %.

3. The process according to claim 1, wherein the inorganic iodide-providing co-catalyst is lithium iodide present in a lithium iodide:rhodium molar ratio of about 1:1 up to a ratio of about 50:1.

4. The process according to claim 1, wherein the process is further characterized by a STY greater than 10 moles/L/hr.

5. The process according to claim 1, wherein the iodide promoter is methyl iodide maintained in said reaction mixture in a concentration of from about 1 to about 20 weight percent.

6. The process according to claim 1, wherein the process is operated with a total inorganic iodide content in the reaction mixture of less than 4.5 weight % and the water content of the reaction mixture is maintained at a level of less than or equal to 5 weight %.

7. The process according to claim 1, wherein the metallic co-stabilizing or rate-promoting composition comprises a single metal compound.

8. The process according to claim 1, wherein the metallic co-stabilizing or rate-promoting composition comprises two metal components.

9. The process according to claim 1, wherein the reaction mixture contains from 250 ppm rhodium to 3000 ppm rhodium.

10. The process according to claim 1, wherein:
   the aqueous reaction mixture is disposed in a pressurized reactor,
   and wherein the homogeneous rhodium-based aqueous catalyst system further comprises
   (v) methyl acetate maintained in said reaction mixture in a concentration of from about 0.5 to about 30 weight percent; and
   (vi) acetic acid;
   and wherein further the step of recovering acetic acid comprises
   providing a stream of the reaction mixture to a flash vessel;
   flashing crude acetic acid product from the reaction mixture to generate a crude product stream including acetic acid, methyl acetate, methyl iodide and water; and purifying the crude product stream to remove methyl acetate, methyl iodide and water therefrom, to obtain a purified acetic acid product.

11. The process according to claim 10, wherein the process is further characterized by a propionic acid concentration of less than 50 parts per million as measured at the flash vessel overhead.

12. The process according to claim 10, wherein a partial pressure of carbon monoxide is maintained above 1 bar in the pressurized reactor.

13. The process according to claim 10, wherein a partial pressure of carbon monoxide is maintained below 1 bar in the flash vessel.

14. The process according to claim 1, wherein:
the inorganic iodide-providing co-catalyst is provided at a molar ratio of inorganic iodide-providing co-catalyst:Rh of less than 70:1; and
the metallic co-stabilizing or rate-promoting composition is present in a metal to rhodium molar ratio of at least 0.5:1 and up to 20:1.

15. The process according to claim 1, wherein the water content of the reaction mixture is maintained at a level of from 0.2 weight % to 5 weight %.

* * * * *